United States Patent
Koike et al.

(10) Patent No.: US 11,471,074 B2
(45) Date of Patent: Oct. 18, 2022

(54) MIDDLE EAR SOUND TRANSMISSION CHARACTERISTICS EVALUATION SYSTEM, MIDDLE EAR SOUND TRANSMISSION CHARACTERISTICS EVALUATION METHOD, AND MEASURING PROBE

(71) Applicants: The University of Electro-Communications, Tokyo (JP); Keio University, Tokyo (JP); Mechano Transformer Corporation, Tokyo (JP); Leadence Corporation, Iruma-gun (JP); Daiichi Medical, Tokyo (JP)

(72) Inventors: Takuji Koike, Tokyo (JP); Yuuka Irie, Tokyo (JP); Sho Kanzaki, Tokyo (JP); Sze Keat Chee, Tokyo (JP); Takenobu Higo, Iruma-gun (JP); Masaaki Hayashi, Tokyo (JP)

(73) Assignees: The University of Electro-Communications, Tokyo (JP); Keio University, Tokyo (JP); Mechano Transformer Corporation, Tokyo (JP); Daiichi Medical, Tokyo (JP); Leadance Corporation, Iruma-gun (JP)

( * ) Notice: Subject to any disclaimer, the term of this patent is extended or adjusted under 35 U.S.C. 154(b) by 790 days.

(21) Appl. No.: 16/260,603

(22) Filed: Jan. 29, 2019

(65) Prior Publication Data
US 2020/0029865 A1 Jan. 30, 2020

Related U.S. Application Data

(63) Continuation of application No. PCT/JP2018/042525, filed on Nov. 16, 2018.

(30) Foreign Application Priority Data

Jul. 30, 2018 (JP) .............................. JP2018-142976

(51) Int. Cl.
A61B 5/12 (2006.01)
A61B 5/00 (2006.01)
(Continued)

(52) U.S. Cl.
CPC ............ *A61B 5/121* (2013.01); *A61B 5/6817* (2013.01); *A61B 5/7203* (2013.01); *H04R 25/606* (2013.01); *H04R 29/00* (2013.01)

(58) Field of Classification Search
CPC ....... A61B 5/0051; A61B 5/121; A61B 5/125; A61B 5/6817; A61B 5/7203; A61B 2562/0219; H04R 25/606; H04R 29/00
(Continued)

(56) References Cited

U.S. PATENT DOCUMENTS 5,776,144 A 7/1998 Leysieffer et al.
9,072,468 B2 * 7/2015 Buchman ............ A61M 5/1723
(Continued)

FOREIGN PATENT DOCUMENTS

FR 2990753 A1 11/2013
JP 2003-290153 A 10/2003
(Continued)

OTHER PUBLICATIONS

T. Koike, M. et al "An apparatus for diagnosis of ossicular chain mobility in humans", 2006, International Journal of Audiology; 45: 121-128 (Year: 2006).*
(Continued)

*Primary Examiner* — Christian Jang
*Assistant Examiner* — Anna Roberts
(74) *Attorney, Agent, or Firm* — DLA Piper LLP (US)

(57) ABSTRACT

A middle ear sound transmission characteristics evaluation system includes a probe; a measuring probe that includes an actuator that vibrates the probe and a force sensor that outputs a voltage in accordance with a reaction force exerted
(Continued)

to the actuator when a tip of the probe is brought into contact with ossicles; an electrode that is installed on or near a round window and detects a potential value of a cochlear microphonic when vibration is applied to the ossicles by the probe; a database that stores a sensor voltage value output by the force sensor before surgical treatment, the potential value detected by the electrode, and surgical details; and a surgical details proposing unit that proposes selected surgical details on the basis of the magnitude of at least one of the sensor voltage value and the potential value measured before surgery with reference to the database.

19 Claims, 22 Drawing Sheets

(51) Int. Cl.
*H04R 25/00* (2006.01)
*H04R 29/00* (2006.01)

(58) Field of Classification Search
USPC .......................................................... 600/599
See application file for complete search history.

(56) References Cited

U.S. PATENT DOCUMENTS

| | | | |
|---|---|---|---|
| 2002/0026125 | A1 | 2/2002 | Leysieffer |
| 2005/0096561 | A1* | 5/2005 | Conn .................. A61B 5/6817 600/559 |
| 2005/0131272 | A1* | 6/2005 | Waldmann ........... H04R 25/606 600/25 |
| 2013/0303941 | A1 | 11/2013 | Porges et al. |
| 2017/0208403 | A1 | 7/2017 | Nakajima |
| 2017/0360364 | A1 | 12/2017 | Heasman et al. |
| 2018/0055908 | A1* | 3/2018 | Petit ........................ A61P 29/00 |
| 2019/0038189 | A1* | 2/2019 | Magnussen ............ A61B 5/126 |

FOREIGN PATENT DOCUMENTS

| | | | |
|---|---|---|---|
| JP | 2003290153 A | * | 10/2003 |
| JP | 2006-136419 A | | 6/2006 |
| WO | 2012/082721 A2 | | 6/2012 |
| WO | 2014/079549 A1 | | 5/2014 |
| WO | 2015/168698 A1 | | 11/2015 |

OTHER PUBLICATIONS

International Search Report dated Feb. 5, 2019, of International Application No. PCT/JP2018/042525, along with an English translation.
Koike, T., "Development of apparatus for measuring ossicular mobility using ear pick", Kanzaki products. Otology Japan, vol. 27, No. 4, Japan Ear Science Society, Oct. 25, 2017, p. 384.
Ebine, R. et al., "Development and performance evaluation of apparatus for measuring ossicular mobility using ear pick", 30th Bio-Engineering Lecture Proceedings, The Japan Society of Mechanical Engineers, Dec. 13, 2017, p. 340.
Reason for Rejection dated May 29, 2019, of counterpart Japanese Application No. 2018-216058, along with an English translation.
Reason for Rejection dated Jul. 29, 2019, of counterpart Japanese Application No. 2018-216058, along with an English translation.
The First Office Action dated Dec. 17, 2021, of counterpart Chinese Patent Application No. 20188003138.3, along with an English translation.
Extended European Search Report dated Apr. 14, 2022, of counterpart European Patent Application No. 18842628.2.
H. Liu et al., "An Incus-Body Driving Type Piezoelectric Middle Ear Implant Design and Evaluation in 3D Computational Model and Temporal Bone," The Scientific World Journal, vol. 2014, pp. 1-8, Jan. 1, 2014, Full article retrieved from the internet.
J. Peacock et al., "Measurement of the Vibration of the Middle Ear Ossicles with Removed Eardrum: A Method for Quantification of Ossicular Fixation," Medical Engineering & Physics, vol. 35, No. 12, pp. 1786-1792, Dec. 1, 2013, Full Article in English retrieved from the internet.
Second Office Action dated Aug. 22, 2022, of counterpart Chinese Patent Application No. 201880003138.3, along with an English translation.

* cited by examiner

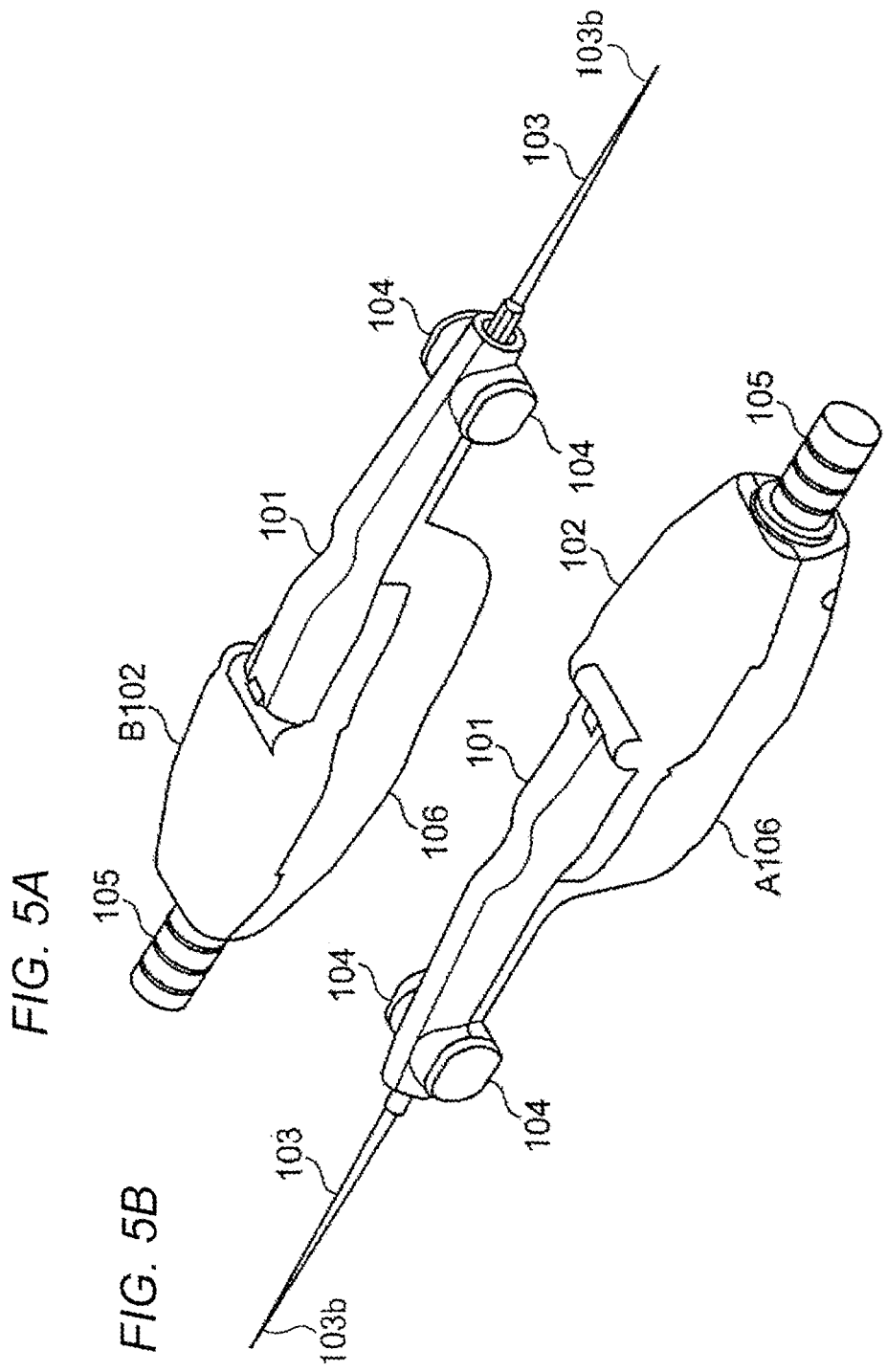

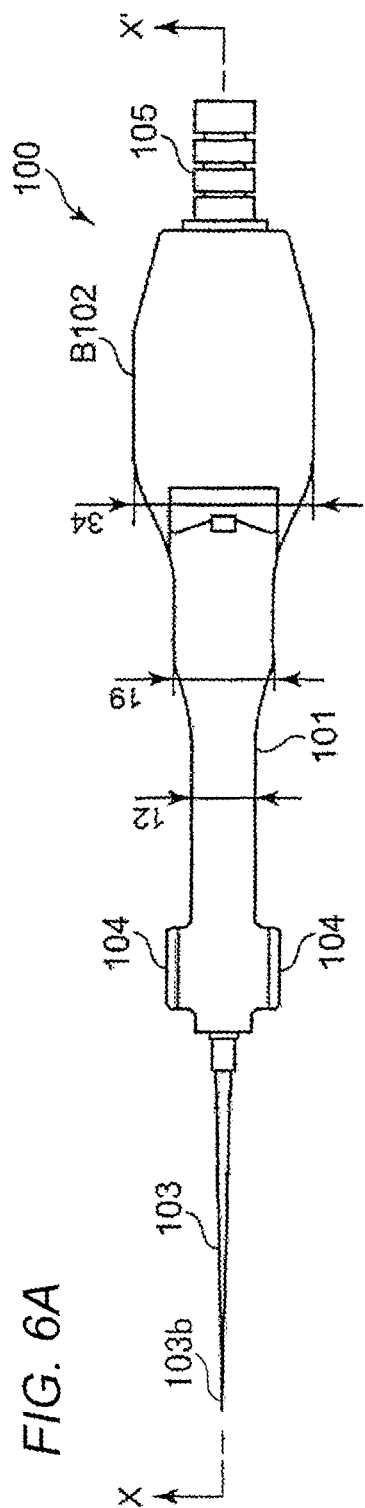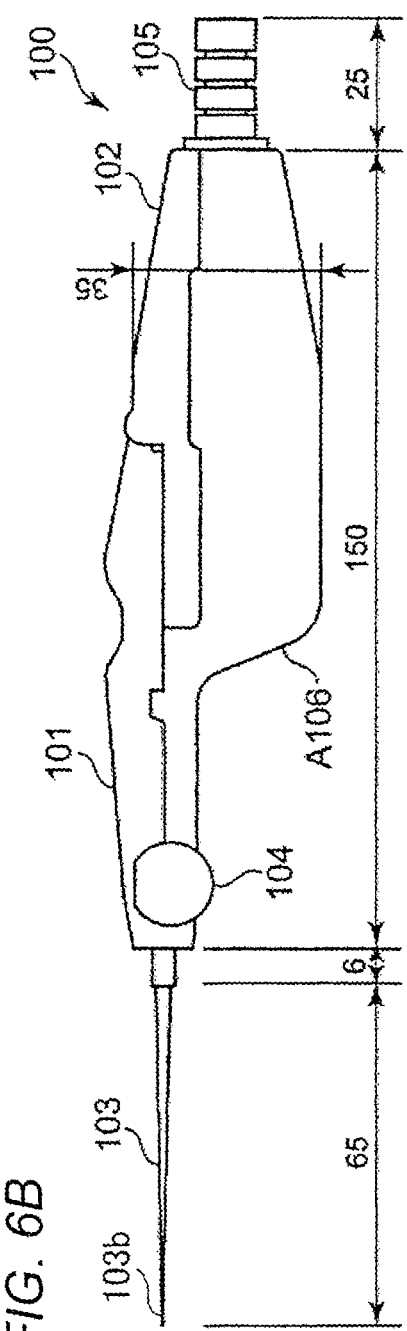
FIG. 6A
FIG. 6B

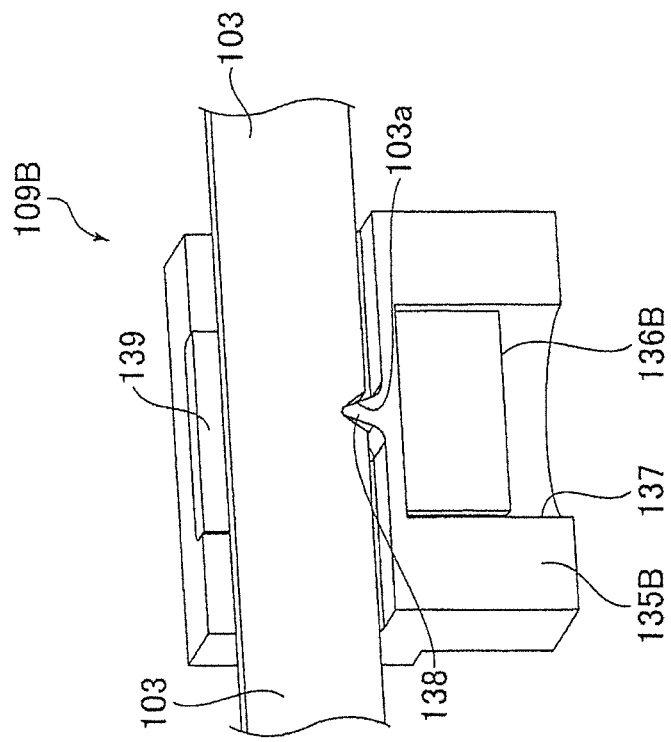
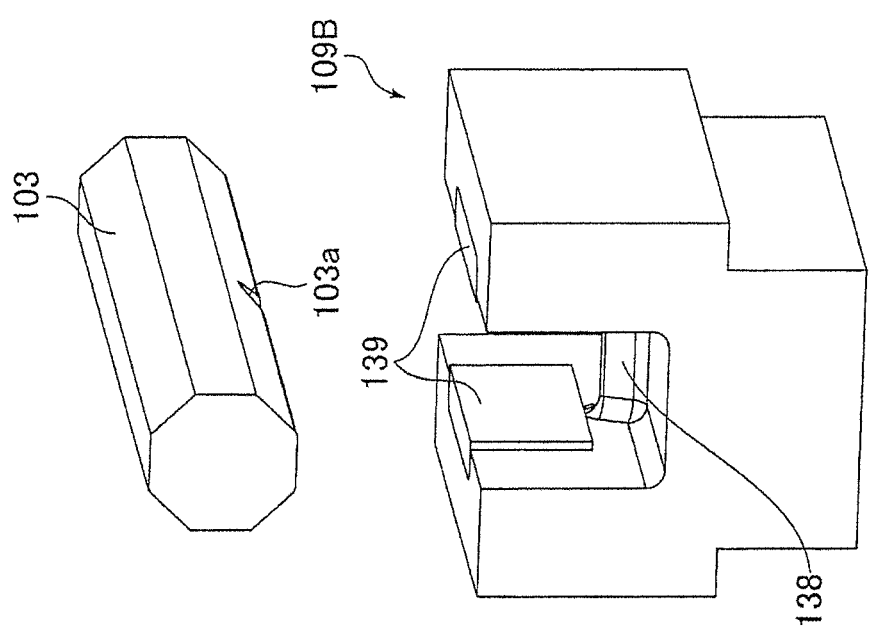

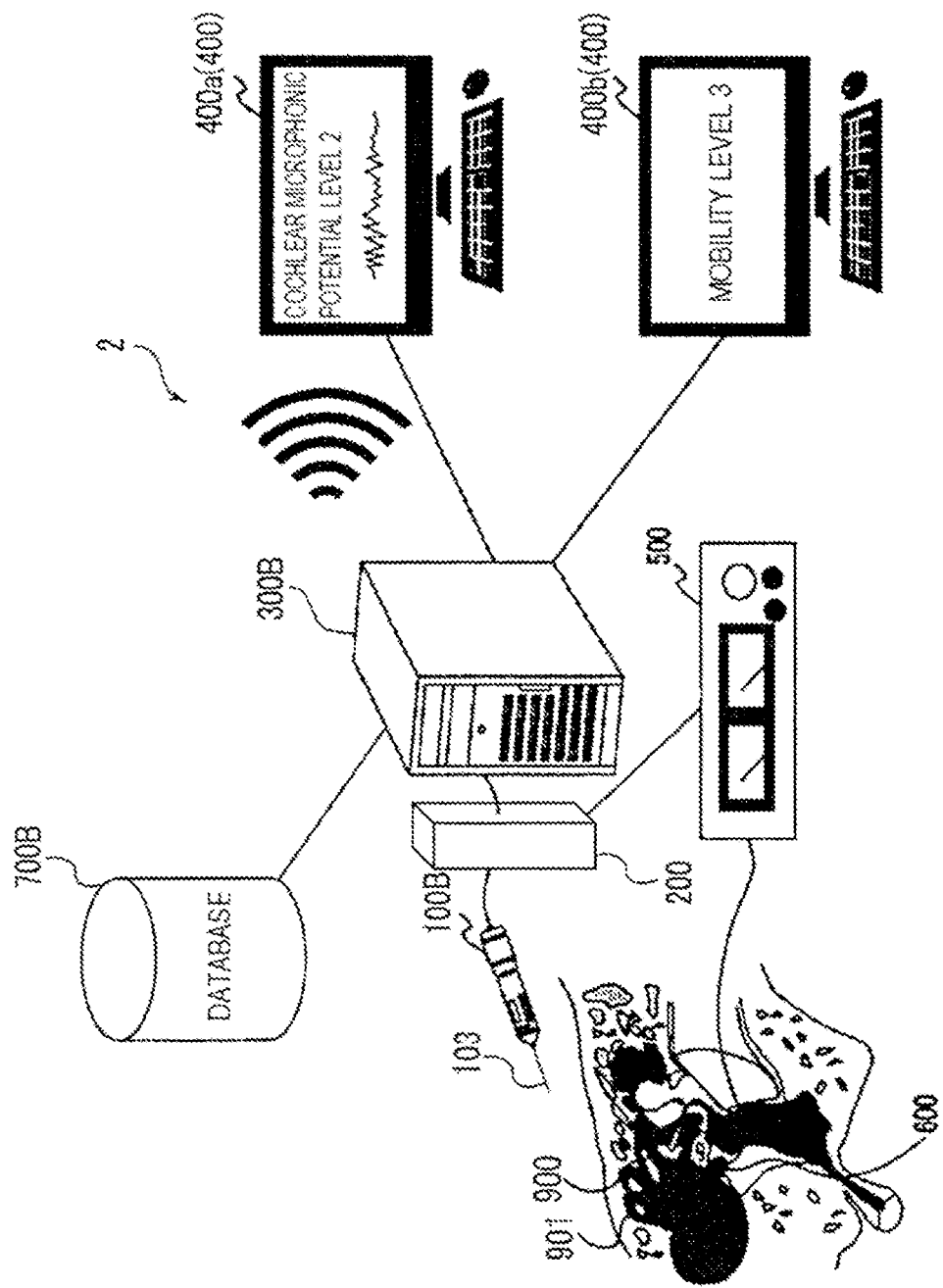

MIDDLE EAR SOUND TRANSMISSION CHARACTERISTICS EVALUATION SYSTEM, MIDDLE EAR SOUND TRANSMISSION CHARACTERISTICS EVALUATION METHOD, AND MEASURING PROBE

TECHNICAL FIELD

This disclosure relates to a middle ear sound transmission characteristics evaluation system and a middle ear sound transmission characteristics evaluation method that evaluates the sound transmission characteristics of the middle ear using ossicular mobility measurement and cochlear microphonic potential measurement, and a measuring probe.

BACKGROUND

Human ears perceive sound in a way that, when sound coming into the external auditory canal causes the eardrum to vibrate, the vibration of the eardrum is transmitted to the cochlea after sequentially passing through the three ossicles, that is, the malleus, incus, and stapes located inside the eardrum. Then, a signal is generated in the cochlea in accordance with the pitch of the sound, and the signal is transmitted to the brain through the cochlear nerves.

Since the ossicles maintain normal mobility in a normal ear, vibration of the eardrum can be appropriately transmitted. However, when one or more ossicles are not able to maintain normal mobility due to, for example, illness or aging, it is not possible to appropriately transmit vibration of the eardrum, and thus hearing loss due to transmission disorder may occur.

Therefore, to restore hearing, middle ear surgery to restore the mobility of the ossicles to the normal state is performed. In that type of middle ear surgery, identification of a fixed site and determination of the degree of fixing necessary to determine an operation type are performed using a method of an operator pushing the ossicles such that they move by operating a probe (see Japanese Unexamined Patent Application Publication No. 2006-136419). In addition, as a method of evaluating the degree to which hearing has been restored through surgery, evaluation of the degree to which the mobility of the ossicles has been restored through palpation using a probe, and evaluation of the degree to which actual sound transmission characteristics have been restored by measuring the hearing after surgery have been performed.

However, in ossicles surgery, it may be difficult to identify a defective site and decide what treatment should be performed, which heavily depends on the experience of the doctor conducting the surgery. Thus, it is difficult for, for example, doctors having little experience to identify a defective site and decide the details of treatment, and there is room for improvement in the method of selecting the details of desired surgery.

Therefore, it could be helpful to provide a middle ear sound transmission characteristics evaluation system and a middle ear sound transmission characteristics evaluation method that make it easier to identify a defective site and select treatment and can propose selected surgical details.

SUMMARY

We thus provide:
(1) A middle ear sound transmission characteristics evaluation system (middle ear sound transmission characteristics evaluation system 1) that includes:

a measuring probe (measuring probe 100) including
a probe (probe 103),
an actuator (actuator 116) that vibrates the probe, and
a force sensor (piezoelectric sensor 117 and charge amplifier 112) that outputs a voltage in accordance with a reaction force exerted to the actuator when a tip (tip 103b) of the probe is brought into contact with ossicles (ossicles 900);
a mobility evaluation unit (mobility evaluation unit 331) that categorizes the mobility of the ossicles into one of a plurality of mobility evaluation levels on the basis of a voltage output from the force sensor;
an electrode (electrode 600) that is installed on a round window or near a round window and detects a cochlear microphonic potential when vibration is applied to the ossicles by the probe;
an amplifier (amplifier 500) that amplifies the detected cochlear microphonic potential;
a vibration transmission efficiency evaluation unit (vibration transmission efficiency evaluation unit 332) that categorizes vibration transmission efficiency of the ossicles into one of a plurality of vibration transmission efficiency evaluation levels on the basis of the amplified cochlear microphonic potential; and
an output unit (output unit 800, sound output unit 340, display device 400) that outputs a value of the mobility evaluation level categorized by the mobility evaluation unit and a value of the vibration transmission efficiency evaluation level categorized by the vibration transmission efficiency evaluation unit.
(2) The middle ear sound transmission characteristics evaluation system described in (1) further includes a database (database 700) that stores the value of the mobility evaluation level and the value of the vibration transmission efficiency evaluation level as evaluation data.
(3) The middle ear sound transmission characteristics evaluation system described in (2), in which the database stores the evaluation data of pre-treatment, intra-treatment, and post-surgical treatment.
(4) The middle ear sound transmission characteristics evaluation system described in any one of (1) to (3), wherein the mobility evaluation unit obtains the magnitude of a specific frequency component of the voltage output from the force sensor and categorizes the mobility of the ossicles into any of the plurality of mobility evaluation levels on the basis of the magnitude.
(5) The middle ear sound transmission characteristics evaluation system described in any one of (1) to (4), wherein the vibration transmission efficiency evaluation unit obtains the magnitude of the specific frequency component of the voltage output from the amplifier and categorizes the vibration transmission efficiency of the ossicles into any of the plurality of vibration transmission efficiency evaluation levels on the basis of the magnitude.
(6) The middle ear sound transmission characteristics evaluation system described in (4), in which the probe is detachably supported by each of a fixation fulcrum and the force sensor at two points that are near the center of gravity and a base end (base end 103c) of the probe, the actuator applies vibration having a constant amplitude with respect to the fulcrum near the center of gravity of the probe, the force sensor includes a piezoelectric sensor (piezoelectric sensor 117) and a charge amplifier (charge amplifier 112), the piezoelectric sensor generates a charge signal by exerting s reaction force to a force exerted by the actuator to the probe from the probe, the charge amplifier converts the generated charge signal into a voltage and outputs the voltage, and the mobility evaluation unit performs frequency analysis on the basis of the voltage output from the measuring probe and obtains the magnitude of the specific frequency component.

(7) The middle ear sound transmission characteristics evaluation system described in (6), in which the probe has a recess (recess 103a) formed near the center of gravity, the fulcrum include a magnet (magnet 136) for fitting to and supporting the recess, and the magnet comes in partial contact with an inner surface of the recess.

(8) The middle ear sound transmission characteristics evaluation system described in (6) or (7), in which the measuring probe includes an elastic body (plate spring 107) that elastically comes in contact with the probe.

(9) The middle ear sound transmission characteristics evaluation system described in any one of (6) to (8), in which the actuator vibrates the probe at a frequency of 5 Hz or higher, and the specific frequency component is a frequency component of 5 Hz or higher.

(10) The middle ear sound transmission characteristics evaluation system described in any one of (6) to (9), in which the measuring probe includes a rigidity/inertial force applying member (lower cover A106) that applies rigidity with which relative positions of the fulcrum and the actuator 116 can be kept constant and an inertial force with which the measuring probe can resist vibration of the actuator to the measuring probe.

(11) A middle ear sound transmission characteristics evaluation method including:

an excitation step (excitation step S10) in which vibration is applied to the ossicles by bringing the tip of a probe that has been vibrated by an actuator in contact with the ossicles, a voltage measurement step (voltage measurement step S12) in which a voltage in accordance with a reaction force to the actuator when the tip of the probe is brought into contact with the ossicles is output, a mobility evaluation step (mobility evaluation step S13) in which the mobility of the ossicles is categorized into any of a plurality of mobility evaluation levels on the basis of the voltage, a cochlear microphonic potential detection step (cochlear microphonic potential detection step S14) in which an electrode is installed on a round window or near the round window and a cochlear microphonic potential generated when vibration is applied to the ossicles in the excitation step is detected, an amplification step (amplification step S15) in which the detected cochlear microphonic potential is amplified, a vibration transmission efficiency evaluation step (vibration transmission efficiency evaluation step S16) in which vibration transmission efficiency of the ossicles is categorized into any of a plurality of vibration transmission efficiency evaluation levels on the basis of the amplified cochlear microphonic potential, and an output step (output step S17) in which the value of the mobility evaluation level categorized in the mobility evaluation step and the value of the vibration transmission efficiency evaluation level categorized in the vibration transmission efficiency evaluation step are output.

BRIEF DESCRIPTION OF THE DRAWINGS

FIGS. 5A and 5B are perspective views illustrating the measuring probe illustrated in FIG. 4.

FIG. 6A is a plan view of the measuring probe illustrated in FIG. 4. FIG. 6B is a side view of the measuring probe illustrated in FIG. 4.

FIG. 11A is a perspective view of a state in which the probe is removed and FIG. 11B is a cross sectional view of a state in which the probe is attached according to a modified example of the fulcrum metal fitting illustrated in FIG. 10.

FIG. 12 is a system diagram illustrating a configuration of a middle ear sound transmission characteristics evaluation system according to a second example.

EXPLANATION OF REFERENCES

Figure 1:
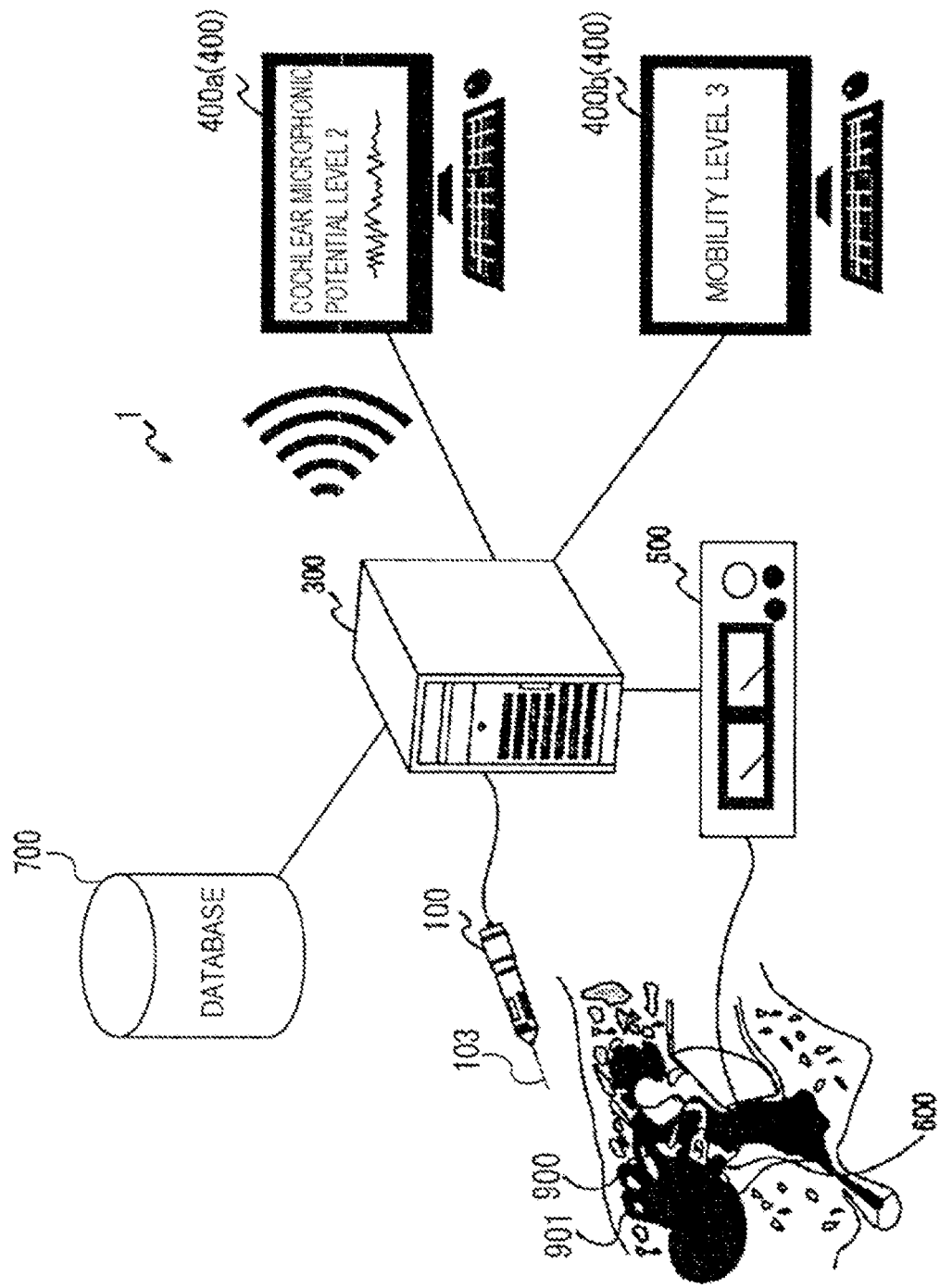
FIG. 1 is a system diagram illustrating a configuration of a middle ear sound transmission characteristics evaluation system according to a first example.

1 Middle ear sound transmission characteristics evaluation system
100 Measuring probe
103 Probe
103a Recess
103b Tip
103c Base end
A106 Lower cover (rigidity/inertial force applying member)
107 Plate spring (elastic body)
109 Fulcrum metal fitting (fulcrum)
112 Charge amplifier (force sensor)
116 Actuator
117 Piezoelectric sensor
136 Magnet 331 Mobility evaluation unit
332 Vibration transmission efficiency evaluation unit
333 Surgical details proposing unit
340 Sound output unit (output unit)
400 Display device (output unit)
500 Amplifier
600 Electrode
700 Database
800 Output unit
900 Ossicles
S10 Excitation step
S12 Voltage measurement step
S13 Mobility evaluation step
S14 Cochlear microphonic potential detection step
S15 Amplification step
S16 Vibration transmission efficiency evaluation step
S17 Output step
S18 Data checking step
S19 Data accumulation step
S20 Surgical details proposing step

DETAILED DESCRIPTION

A middle ear sound transmission characteristics evaluation system includes a measuring probe that includes a probe, an actuator that vibrates the probe and a force sensor that outputs a voltage in accordance with a reaction force exerted to the actuator when a tip of the probe is brought into contact with the ossicles; an electrode that is installed on a round window or near a round window and detects a potential value of a cochlear microphonic when vibration is applied to the ossicles by the probe; a database that stores a sensor voltage value output by the force sensor before surgical treatment, the potential value detected by the electrode, and surgical details; and a surgical details proposing unit that proposes selected surgical details on the basis of the magnitude of at least a sensor voltage value and a potential value measured before surgery with reference to the sensor voltage values, potential values, and surgical details stored in the database.

The database may store symptoms assumed in the ossicles and mobility analysis values calculated from numerical simulations as the values of the mobility at the times of the symptoms, and the surgical details proposing unit may propose selected surgical details on the basis of the magnitude of a sensor voltage value measured before surgery with reference to the assumed symptoms and the mobility analysis values stored in the database.

The database may further store sensor voltage values output by the force sensor during and after surgical treatment and potential values detected by the electrode, and the surgical details proposing unit may further propose selected surgical details on the basis of the magnitude of at least one of sensor voltage values and potential values measured before, during, and after the treatment with reference to the sensor voltage values, the potential values, and the surgical details stored in the database.

A mobility evaluation unit that categorizes the mobility of the ossicles into one of a plurality of mobility evaluation levels on the basis of a sensor voltage value output from the force sensor, an amplifier that amplifies a detected potential value of the cochlear microphonic, a vibration transmission efficiency evaluation unit that categorizes vibration transmission efficiency of the ossicles into one of a plurality of vibration transmission efficiency evaluation levels on the basis of the amplified potential value, and an output unit that outputs the value of the mobility evaluation level categorized by the mobility evaluation unit and the value of the vibration transmission efficiency evaluation level categorized by the vibration transmission efficiency evaluation unit may be provided, and the database may store the value of the mobility evaluation level and the value of the vibration transmission efficiency evaluation level.

The mobility evaluation unit may obtain the magnitude of a specific frequency component of the voltage output from the force sensor and categorize the mobility of the ossicles into one of the plurality of mobility evaluation levels on the basis of the magnitude.

The actuator may vibrate the probe at a frequency of 5 Hz or higher, and the mobility evaluation unit may set the specific frequency component as a frequency component of 5 Hz or higher.

The vibration transmission efficiency evaluation unit may obtain the magnitude of the specific frequency component of the voltage output from the amplifier and categorize the vibration transmission efficiency of the ossicles into one of the plurality of vibration transmission efficiency evaluation levels on the basis of the magnitude.

A middle ear sound transmission characteristics evaluation method may include an excitation step in which vibration is applied to the ossicles by bringing the tip of a probe that has been vibrated by an actuator in contact with the ossicles; a voltage measurement step in which a voltage in accordance with a reaction force to the actuator when the tip of the probe is brought into contact with the ossicles is output; a cochlear microphonic potential detection step in which an electrode is installed on a round window or near the round window and a potential value of a cochlear microphonic generated when vibration is applied to the ossicles in the excitation step is detected; a data accumulation step in which a sensor voltage value output in the voltage measurement step before surgical treatment, the potential value detected in the cochlear microphonic potential detection step, and surgical details are stored in a database; and a surgical details proposing step in which selected surgical details are proposed on the basis of at least one of the sensor voltage value and the potential value measured before surgery with reference to the sensor voltage values, the potential values, and the surgical details stored in the database.

A measuring probe includes a probe, a fulcrum metal fitting that supports the probe, an actuator that vibrates the probe, and a force sensor that outputs a voltage in accordance with a reaction force to the actuator when the tip of the probe is brought into contact with ossicles, the actuator applies vibration having a constant amplitude with respect to the fulcrum near the center of gravity of the probe, the force sensor includes a piezoelectric sensor and a charge amplifier, the piezoelectric sensor converts a reaction force to a force exerted by the actuator via the probe to the ossicles into a charge signal, and the charge amplifier converts the charge signal into a voltage and outputs it.

The actuator may vibrate the probe at a frequency of 5 Hz or higher.

A rigidity/inertial force applying member that applies rigidity with which relative positions of the fulcrum and the actuator can be kept constant and an inertial force with which the measuring probe can resist vibration of the actuator to the measuring probe may also be included.

The probe may be detachably supported by a fixation fulcrum and the force sensor at two points that are near the center of gravity and the base end of the probe, the probe may have a recess formed near the center of gravity, the fulcrum metal fitting may include a support unit that supports the probe while fitting into the recess and attracts the probe using a magnetization force.

An elastic body that elastically comes in contact with the probe may be provided, and the probe may be biased to the magnet by the elastic body.

The inner surface of the recess may have a spherical surface shape and the magnet may have a spherical body shape.

The probe may be detachably supported by the fixation fulcrum and the force sensor at two points that are near the center of gravity and the base end of the probe, the inner surface of the recess may have a triangular shape in a longitudinal cross section view in the direction in which the probe extends, and the magnet may have a triangular shape in the longitudinal cross section view.

The fulcrum metal fitting may be formed to cover the probe from both sides in the left-right direction, a rotational shaft that extends orthogonal to the probe in a top view and pivotably supports the probe in the top-bottom direction may be provided, and the rotational shaft may be disposed to penetrate the probe and the fulcrum metal fitting.

A metal frame including a housing recess in which the fulcrum metal fitting is housed while supporting the probe may be provided, and a fixing magnet that fixes the fulcrum metal fitting may be built into the metal frame.

A cover having an opening formed to allow the tip of the probe to protrude outward may be provided, and a pipe-shaped metal cap coaxially formed with the opening may be detachably attached to the opening.

An actuator case that covers the actuator may be provided, and the inner side of the actuator case may have a watertight structure.

According to a middle ear sound transmission characteristics evaluation system and a middle ear sound transmission characteristics evaluation method, since vibration transmission efficiency of ossicles can be quantitatively evaluated during middle ear surgery performed using a probe, the middle ear surgery can be performed while the degree of hearing restoration can be quantitatively determined.

A sensor voltage value output by the force sensor before treatment, a potential value detected by an electrode, and the surgical details are stored in a database. In addition, a surgical details proposing unit proposes selected surgical details on the basis of the value of at least one of a sensor voltage value and a potential value measured before the surgery with reference to the sensor voltage values, potential values, and surgical details stored in the database. Thus, identification of a defective site and selection of treatment become easy by utilizing past surgical experience, and selected surgical details can be proposed.

First Example

A first example will be described below with reference to the drawings.
Configuration of Middle Ear Sound Transmission Characteristics Evaluation System 1

FIG. 1 is a system diagram illustrating an example of a configuration of a middle ear sound transmission characteristics evaluation system 1.

The middle ear sound transmission characteristics evaluation system 1 includes a measuring probe 100, an information processing device 300, display devices 400 (400a and 400b), an amplifier 500, an electrode 600, and a database 700 as illustrated in FIG. 1. Although only one information processing device 300 is illustrated in FIG. 1, there may be a plurality of information processing devices 300. In addition, although the two display device 400a and 400b are illustrated in FIG. 1 as the display devices 400, there may be one or three or more. Display devices will be collectively referred to as display devices 400 below when there is no particular need to distinguish them from each other. In addition, the display devices 400 and a sound output unit 340 of the information processing device 300, which will be described below, of the middle ear sound transmission characteristics evaluation system 1 will be collectively referred to as an output unit 800 as a unit that performs output (display, sound output and the like) of evaluation results of mobility and vibration transmission efficiency of ossicles 900.

Figure 3:
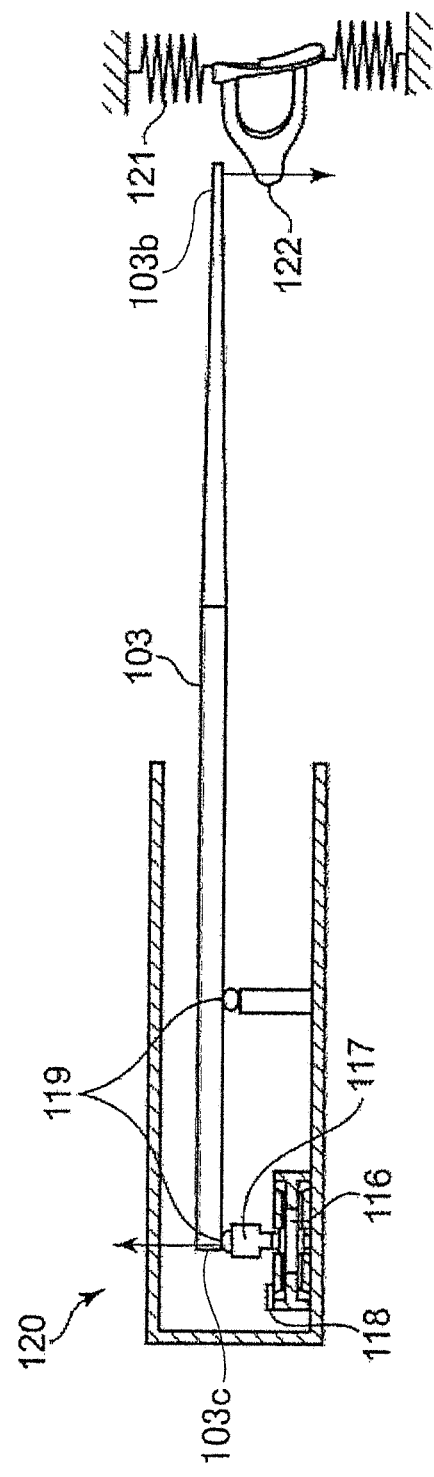
FIG. 3 is a conceptual diagram illustrating the concept of an internal structure of a first structural example of a measuring probe.

The measuring probe 100 includes a probe 103 that serves as a vibration exciter to contact with and impart vibration to the ossicles 900, an actuator 116 (FIG. 3) that vibrates the probe 103, and a force sensor that outputs a voltage in accordance with a reaction force exerted to the actuator 116 when the probe 103 is brought into contact with the ossicles 900 (a piezoelectric sensor 117 and a charge amplifier 112) (FIG. 3).

The information processing device 300 is computer equipment connected to the measuring probe 100, the display devices 400, the amplifier 500, the database 700 and the like in a wired or wireless manner, and receives an information processing request from such peripheral devices and equipment and performs information processing. The information processing device 300 may be general-purpose computer equipment or dedicated computer equipment for the middle ear sound transmission characteristics evaluation system 1.

The display devices 400 are connected to the information processing device 300 and may be any devices as long as they are display devices that display display information output from the information processing device 300 on screens. The display devices 400 display an evaluation result for the mobility of the ossicles 900 evaluated by the information processing device 300 (the value of a categorized mobility evaluation level) and an evaluation value of vibration transmission efficiency of the ossicles 900 (the value of a categorized vibration transmission efficiency evaluation level).

The amplifier 500 may be amplifier equipment such as a differential amplifier that amplifies a cochlear microphonic potential measured by the electrode 600.

The electrode 600 can be installed at or near the round window, and may be an electrode that can measure a cochlear microphonic potential (CM).

The database 700 stores an evaluation result for the mobility of the ossicles 900 evaluated by the information processing device 300 (the value of a mobility evaluation level) and an evaluation result for vibration transmission efficiency of the ossicles 900 (the value of a vibration transmission efficiency evaluation level) as evaluation data. The database 700 stores evaluation data of pre-treatment, intra-treatment, and post-surgical treatment.

The middle ear sound transmission characteristics evaluation system 1 configured as described above causes the probe 103 of the measuring probe 100 to vibrate, and inputs a reaction force exerted to the measuring probe 100 when it contacts the ossicles 900 which are a measurement object to the information processing device 300 as a voltage. The information processing device 300 evaluates the mobility of the ossicles 900 on the basis of the input voltage. More specifically, the information processing device 300 categorizes the mobility of the ossicles 900 into any of a plurality of mobility evaluation levels on the basis of the voltage output from the measuring probe 100. In addition, the information processing device 300 causes the display device 400b to display the value of the categorized mobility evaluation level.

In the example of FIG. 1, "3" is displayed as the value of the mobility evaluation level on the display device 400b. When it is assumed that, for example, there are five mobility evaluation levels, for example, "1" to "5" and "5" represents the evaluation result for the best mobility, "4," "3," "2," and "1" can be set to represent the evaluation results of decreasing mobility as the values become smaller. In this example, "1" represents the evaluation result for the worst mobility (complete fixing). By making the evaluation results of the mobility of the ossicles 900 be represented by the values of the mobility evaluation levels as described above, an operator can quantitatively ascertain the degree of mobility of the ossicles 900 before and during surgery, and thus can determine a procedure or the like with efficiency. In addition, according to the above-described configuration, the mobility of the ossicles 900 can be easily diagnosed during surgery by displaying the evaluation result for the mobility of the ossicles 900 on the screen using a graph together with the value of the mobility evaluation level and informing the operator of the result using sound if necessary.

In addition, the middle ear sound transmission characteristics evaluation system 1 configured as described above brings the measuring probe 100 in contact with the eardrum, the ossicles 900, artificial ossicles which are inserted instead of the ossicles 900 or the like and imparts vibration thereto with the electrode 600 installed in the round window 901, measures a cochlear microphonic potential occurring in the electrode 600 when the vibration is imparted, amplifies the potential using the amplifier 500, and inputs the amplification result to the information processing device 300. The information processing device 300 categorizes the vibration transmission efficiency of the ossicles 900 into any of a plurality of vibration transmission efficiency evaluation levels on the basis of the input potential. Then, the information processing device 300 causes the display device 400a to display the value of the categorized vibration transmission efficiency evaluation level.

In the example of FIG. 1, "2" is displayed on the display device 400a as the value of a cochlear microphonic potential level. When it is assumed that there are five cochlear microphonic potential levels, for example, "1" to "5" and "5" represents the evaluation result for the highest cochlear microphonic potential, "4," "3," "2," and "1" can be set to represent the evaluation results of the lower cochlear microphonic potential as the values become smaller. In this example, "1" represents the evaluation result for the lowest cochlear microphonic potential. As described above, sound transmission characteristics of the middle ear can be quantitatively evaluated during surgery by indicating the evaluation result for the cochlear microphonic potential of the ossicles 900 with numerical values representing the cochlear microphonic potential evaluation levels as described above. Thus, when the operator ascertains that the value of a cochlear microphonic potential evaluation level reaches a predetermined value or higher (e.g., "4" or larger) during the surgery, he or she can determine that the hearing has been restored and end the surgery. Accordingly, the risk of revision surgery is reduced.

In addition, the middle ear sound transmission characteristics evaluation system 1 configured as described above stores the evaluation result evaluated by the information processing device 300, that is, the evaluation result for the mobility of the ossicles 900 (the value of the mobility evaluation level) and the evaluation result for the vibration transmission efficiency of the ossicles 900 (the value of the vibration transmission efficiency evaluation level) in the database 700 as evaluation data. When the number of clinical trials increases, evaluation data of a large number of patients is stored in the database 700. By accumulating the evaluation data of a large number of patients in the database 700 as described above, the operator can determine the desired procedure and the like and then collect useful information that can be determination resources from the database 700. In particular, since the evaluation data (intra-surgical evaluation data) of the mobility and the vibration transmission efficiency of the ossicles 900 during the surgery can be obtained, the database 700 including data regarding procedures, and pre-surgical, intra-surgical, and post-surgical evaluation data can be constructed. With reference to the database 700 before, during, and after the surgery, a doctor can get support for diagnosis and treatment. In addition, by making the database 700 big data and employing a user interface created by incorporating the artificial intelligence (AI) technology into the data reference system, the doctor can get more appropriate and advanced support for diagnosis and treatment.

In addition, according to the middle ear sound transmission characteristics evaluation system 1 configured as described above, since a large amount of evaluation results of the mobility of the ossicles 900 is stored in the database 700 as numerical values, that is, values of the mobility evaluation levels when the number of clinical trials is large, statistical processing may be performed on the basis of the large amount of data stored in the database 700, and thus the values of the mobility evaluation levels can be standardized as evaluation indices of the mobility of the ossicles 900.

In addition, according to the middle ear sound transmission characteristics evaluation system 1 configured as described above, since a large amount of evaluation results of vibration transmission efficiency of the ossicles 900 is stored in the database 700 as numerical values, that is, values of vibration transmission efficiency evaluation levels when the number of clinical trials is large, statistical processing may be performed on the basis of the large amount of data stored in the database 700 and thus the values of the vibration transmission efficiency evaluation levels can be standardized as evaluation indices of vibration transmission efficiency of the ossicles 900.

In addition, according to the middle ear sound transmission characteristics evaluation system 1 configured as described above, pre-surgical, intra-surgical, and post-surgical evaluation data can be stored in the database 700 together with data regarding procedures. Since a large amount of pre-surgical, intra-surgical, and post-surgical evaluation data and data regarding procedures are gradually stored in the database 700 as the number of clinical trials increases, it is possible to cause a machine learning system to learn how to determine desired procedures using the large amount of data stored in the database 700. If learning by the machine learning system reaches a practical level, it is possible to realize a middle ear surgery support system that presents an desired procedure on the basis of a learning result before or during the middle ear surgery. The machine learning system used in learning of determination of a desired procedure may be a machine learning system dedicated to the middle ear sound transmission characteristics evaluation system 1 or a machine learning system using a general-purpose machine learning application programming interface (API).

Configuration of Information Processing Device 300

A configuration of the information processing device 300 will be described below in detail.

Figure 2:
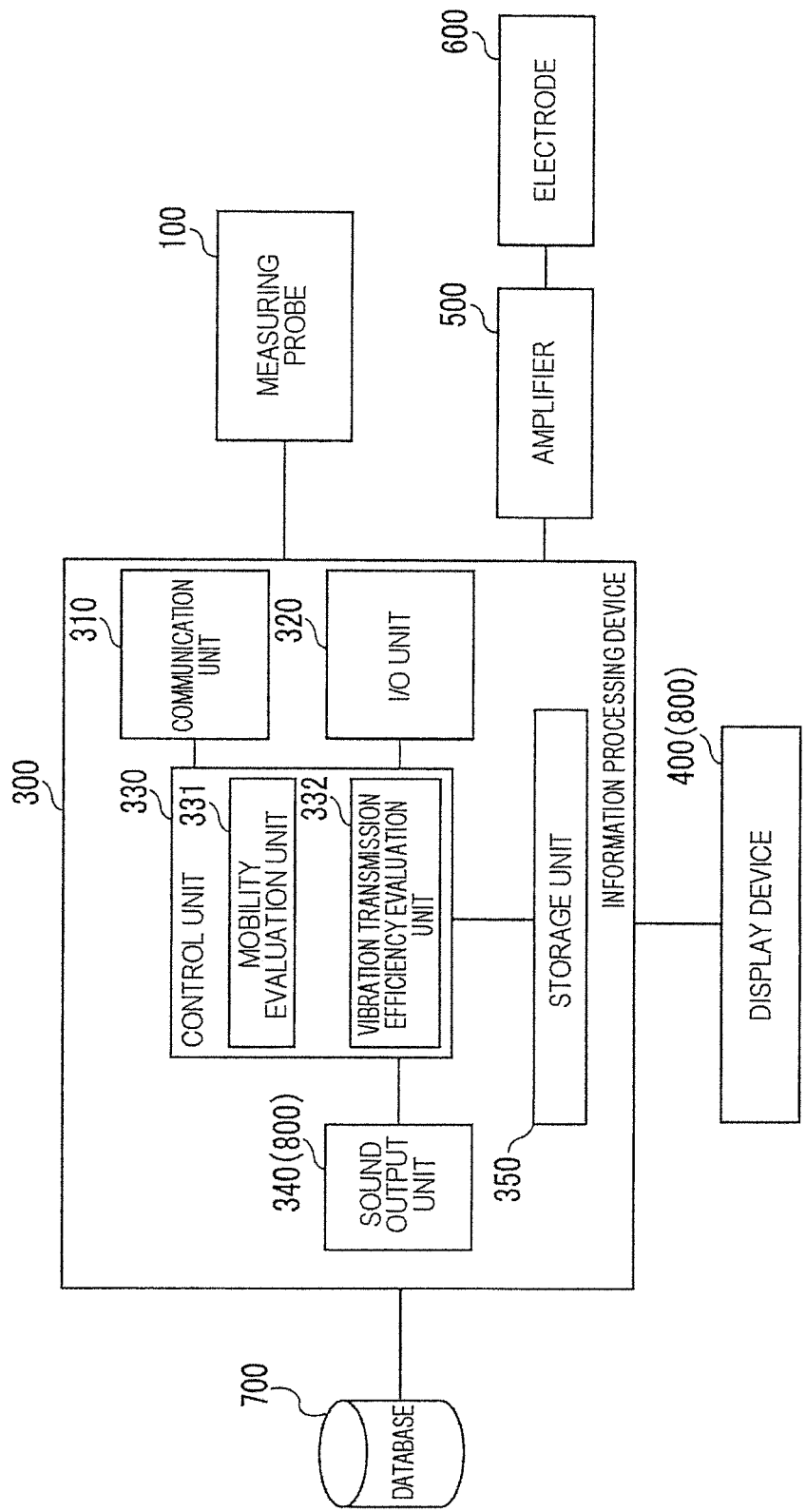
FIG. 2 is a block diagram illustrating a functional configuration of the middle ear sound transmission characteristics evaluation system illustrated in FIG. 1.

FIG. 2 is a block diagram illustrating an example of a configuration of the information processing device 300. The information processing device 300 is provided with a communication unit 310, an I/O unit 320, a control unit 330, a sound output unit 340, and a storage unit 350 as illustrated in FIG. 2.

The communication unit 310 has a function of executing communication (transmission and reception of various messages and the like) with a peripheral device and other information processing devices via a network under control of the control unit 330. Specifically, the communication unit 310 transmits messages transferred from each unit to another device, receives messages from another device, and transfers the received messages to other units via the network under control of the control unit 330. The communication may be performed in a wired or wireless manner, and may use any communication protocol as long as it allows devices to execute mutual communication.

Furthermore, the communication may be subject to encryption processing to ensure security. The "messages" mentioned here include text, images (photos and illustrations), sound, moving images, and the like, and information attached to these (information on date, position and the like attached to text, images, sound, and moving images).

The I/O unit 320 has a function of connecting to other equipment in a wired or wireless manner, another device, or a medium under control of the control unit 330. The I/O unit 320 specifically refers to a connection device for Wireless Fidelity (Wi-Fi), High-Definition Multimedia Interface (HDMI; registered trademark), a Universal Serial Bus (USB), a power connector, an inter-integrated circuit (I2C) or the like.

The control unit 330 is a processor having a function of controlling each unit. The control unit 330 is provided with a mobility evaluation unit 331 and a vibration transmission efficiency evaluation unit 332. The control unit 330 causes each unit to operate in accordance with a program and data stored in the storage unit 350.

The mobility evaluation unit 331 performs FFT analysis on the basis of a voltage output from the measuring probe 100 and thereby obtains a specific frequency component value. "FFT analysis" refers to analysis using a fast Fourier transform in which a component value of each frequency can be analyzed and obtained. The mobility evaluation unit 331 specifically includes an Analog/Digital converter "AD converter", and the AD converter converts a voltage output from the measuring probe 100 into voltage information of a digital signal and performs FFT analysis on the voltage information. As the AD converter, an AD conversion circuit built into the information processing device 300 may be used, or an external AD converter may be used.

In this example, the measuring probe 100 is assumed to be used as a handpiece held by an operator in his or her hand for measurement during surgery, and thus in that case, it is necessary to consider the influence of hand shake thereon. To minimize the influence of hand shake on the voltage output from the measuring probe 100, a specific frequency component value of the measuring probe is set to 5 Hz or higher as an example. In addition, in consideration of the audible range, an excitation frequency of vibration that the measuring probe 100 applies to the ossicles 900 is set to more preferably 20 Hz that is the lower limit of the audible range. At this time, the mobility evaluation unit 331 obtains a component value of voltage information equivalent to the excitation frequency of the vibration that the actuator 116 applies to the probe 103 (input frequency to the actuator 116) as a corresponding specific frequency component value. Specifically, when the mobility evaluation unit 331 sets an excitation frequency of the actuator 116 to 20 Hz, for example, the frequency component value of 20 Hz of each waveform of voltage information is obtained as the specific frequency component value. Accordingly, if the frequency is increased up to the audible range, there is a possibility of causing a cochlea disorder or the like, but it is possible to reduce the influence of hand shake without increasing the frequency up to the audible range. In other words, since the influence of hand shake can be excluded from the voltage output from the measuring probe 100 through FFT analysis performed by the mobility evaluation unit 331, the measurement can be performed while the operator is holding the measuring probe 100 in his or her hand, and thus measurement can be simple during surgery.

With respect to FFT analysis by the mobility evaluation unit 331, the mobility of the stapes 122 and a calibrator simulating the ligament 121 to support the stapes as illustrated in FIG. 3 will be described using the result of the mobility measured by the measuring probe 100. As a result of measuring the calibrator using the measuring probe 100, when the mobility of the calibrator decreases (a spring constant increases), the component of 20 Hz that is the result for FFT analysis increases. The mobility of the ossicles 900 is quantified with the increased amount. Although the frequency component appearing at a frequency of 5 Hz or lower is attributable to hand shake, it can be clearly distinguishable from that of 20 Hz, and thus the mobility of the ossicles 900 can be evaluated with little influence of hand shake even in measurement using the measuring probe 100 in the hand.

The mobility evaluation unit 331 evaluates mobility (compliance) of the ossicles 900 on the basis of a specific frequency component value. Specifically, the mobility evaluation unit 331 evaluates the degree of fixing of the ossicles 900 on the basis of the magnitude of compliance at the frequency component of 20 Hz equal to the excitation frequency of vibration such as rotational vibration that the measuring probe 100 applies to the ossicles 900 (equal to a frequency input to the actuator 116). Specifically, in this example, the mobility evaluation unit 331 categorizes the mobility of the ossicles 900 into any of five mobility evaluation levels ("1" to "5") on the basis of the magnitude of compliance at the frequency component of 20 Hz.

Mobility (compliance) C of the ossicles 900 can be obtained from formula (1) by setting displacement applied by the actuator 116 to the ossicles 900 to D [unit: m] and the reaction force when the actuator 116 applies the displacement to the ossicles 900 to P (unit: N):

$$C = D/P \qquad (1).$$

The vibration transmission efficiency evaluation unit 332 performs FFT analysis on the basis of the voltage output from the amplifier 500 when the measuring probe 100 vibrates the ossicles 900, thereby obtains a cochlear microphonic potential of a specific frequency component, and evaluates vibration transmission efficiency of the ossicles 900 on the basis of the magnitude of the cochlear microphonic potential. Specifically, in this example, the vibration transmission efficiency evaluation unit 332 categorizes the vibration transmission efficiency of the ossicles 900 into any of the five vibration transmission efficiency evaluation levels ("1" to "5") on the basis of the magnitude of the cochlear microphonic potential of a frequency component that is equal to the frequency of the vibration input from the measuring probe 100 to the ossicles 900. The frequency of the vibration input from the measuring probe 100 to the ossicles 900 is a frequency included in a normal audible range, for example, from 125 Hz to 8000 Hz.

The control unit 330 outputs the evaluation results (the values of the mobility evaluation level and the vibration transmission efficiency evaluation level) from the mobility evaluation unit 331 and the vibration transmission efficiency evaluation unit 332 to the database 700 and the display devices 400 via the I/O unit 320.

The sound output unit 340 has a function of outputting sound under control of the control unit 330. The sound output unit 340 can output the evaluation results (the values of the mobility evaluation level and the vibration transmission efficiency evaluation level) from the mobility evaluation unit 331 and the vibration transmission efficiency evaluation unit 332 as sound. The sound output unit 340 may be a speaker built into the information processing device 300 or an external sound output device.

The storage unit 350 has a function of storing various programs, data, and parameters necessary to operate the information processing device 300 under control of the control unit 330. The storage unit 350 includes specifically, for example, a main memory device such as a ROM or a RAM, an auxiliary memory device such as a non-volatile memory, or any of various recording media such as a hard disc drive (HDD), a solid state drive (SSD), or a flash memory. The storage unit 350 may store, for example, the voltage output from the measuring probe 100 as voltage information of the digital signal converted into the digital signal by the AD converter (not illustrated) under control of the control unit 330.

Configuration of the Measuring Probe 100

First Structural Example

A measuring probe 100 according to a first structural example includes a probe 103 and an attachment 120 as illustrated in FIG. 3. In addition, the attachment 120 includes an actuator 116, a piezoelectric sensor 117, a strain gauge 118, and probe fixing magnets 119. FIG. 3 illustrates a state in which the probe 103 is attached to the attachment 120. In FIG. 3, the stapes 122 and the ligament 121 constituting the ossicles 900 are modeled for the sake of description.

Specifically, an otological probe may be used for the probe 103. If the probe 103 that is used in actual otological surgery and the like is used, operators can measure a reaction force of the ossicles 900 without feeling discomfort. Specifically, a piezoelectric actuator with a displacement magnification mechanism for driving the probe 103 may be used for the actuator 116. For the piezoelectric sensor 117, specifically, piezo-type piezoelectric ceramics or the like may be used.

The probe 103 is detachably supported by each of a fixation fulcrum and the piezoelectric sensor 117 at two points that are near the center of gravity and a base end 103c of the probe, and the probe fixing magnets 119 are used at the support units. By configuring the probe 103 to be fixed to the attachment 120 as described above, detachment of the probe 103 is easy and, for example, only the probe 103 can be replaced or subjected to sterilization treatment, and thus sanitation can be improved.

Specifically, the measuring probe 100 brings, for example, a side of the tip 103b of the probe 103 in contact with the ossicles 900 and applies vibration such as rotational vibration having a constant amplitude or the like to the probe 103 using the actuator 116 with respect to the fulcrum near the center of gravity, measures the force imparted by the actuator 116 (i.e., a reaction force from the probe 103) using the piezoelectric sensor 117, and then outputs a voltage. Since the motion of the probe 103 caused by the actuator 116 is similar to a motion performed by an operator during normal measurement in the above-described configuration, the reaction force of the ossicles 900 can be measured without discomfort.

More specifically, the measuring probe 100 vibrates the probe 103 at the frequency of 20 Hz with the actuator 116, and when the tip 103b of the probe 103 is brought into contact with the stapes 122 constituting the ossicles 900, the reaction force exerted to the actuator 116 is measured by the piezoelectric sensor 117, and then a voltage is output. Since it is better for displacement given to the ossicles 900 to be as minute as possible from the viewpoint of protection of the cochlea, displacement given by the actuator 116 of the measuring probe 100 is set to 40 μm or smaller to make it the same degree as in an actual surgical technique, the displacement is amplified using a charge amplifier (not illustrated), and thereby the output voltage becomes proportional to the measured reaction force. The displacement given by the actuator 116 is measured by the strain gauge 118.

Second Structural Example

Figure 4:
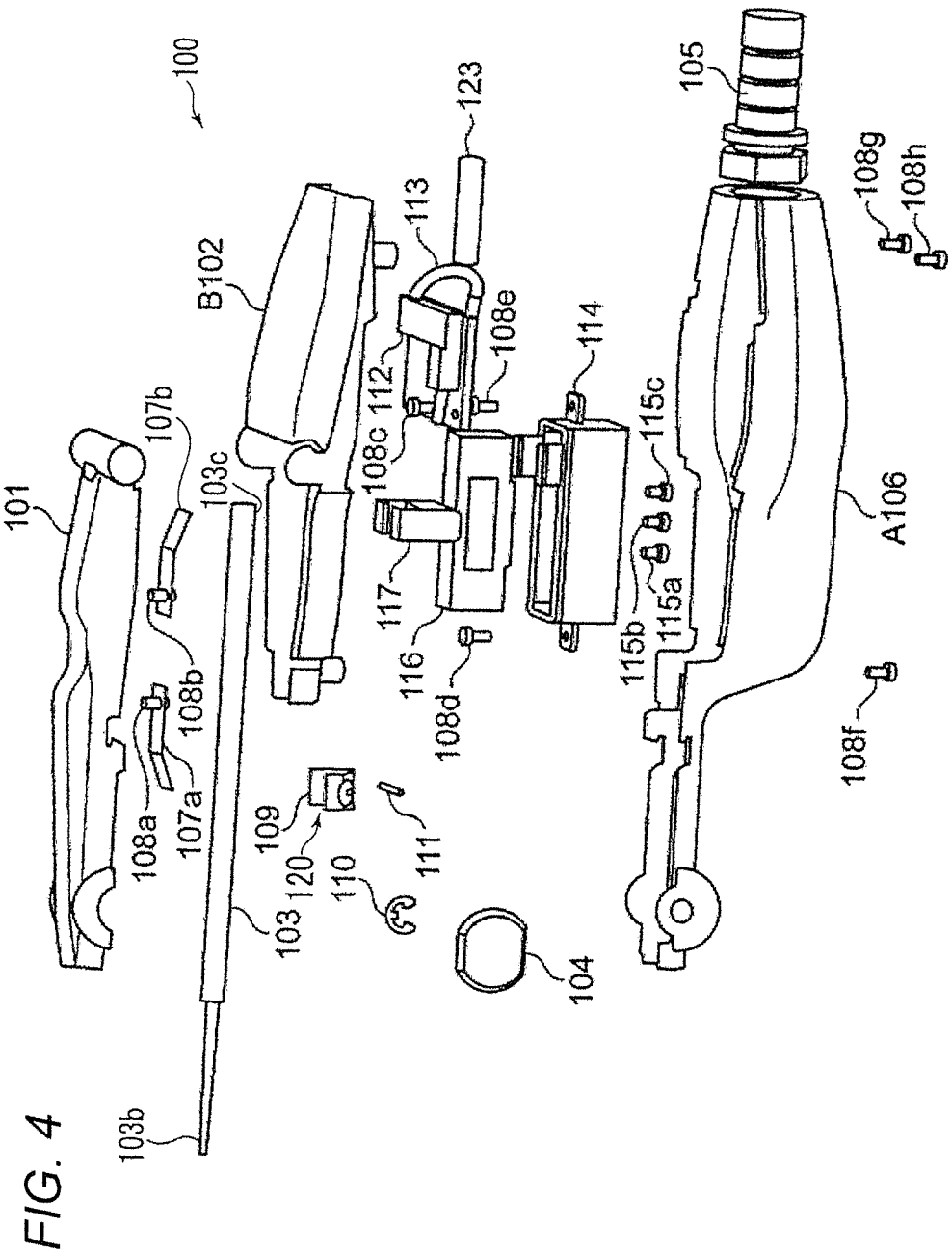
FIG. 4 is an exploded perspective view illustrating a second structural example of the measuring probe.

The measuring probe 100 according to a second structural example includes a first upper cover 101, a second upper cover B102, a probe 103, a locking knob 104, a code bush 105, the lower cover A106, plate springs 107 (107a and 107b), tapping screws 108 (108a, 108b, 108c, 108d, 108e, 108f, 108g, and 108h), a fulcrum metal fitting 109, an E ring 110, an actuator 116, a charge amplifier 112, codes 113 and 123, an actuator holder 114, standard screws 115 (115a, 115b, and 115c), a piezoelectric sensor 117, and a fulcrum fitting fixing pin 111 as illustrated in FIG. 4. In the measuring probe 100 according to the second structural example, the attachment 120 includes the fulcrum metal fitting 109, the actuator 116, and the piezoelectric sensor 117.

The probe 103 is formed in an elongated rod shape. For the probe 103, specifically, an otological probe or the like may be used, and the probe is placed at the fulcrum metal fitting 109 that serves as a fixation fulcrum and the piezoelectric sensor 117 that is attached to the actuator 116, and thereby is supported by and attached to those components. Accordingly, the probe 103 that serves as an otological probe to be used in normal surgery may only be placed at the fulcrum metal fitting 109 and the piezoelectric sensor 117 that is attached to the actuator 116 (i.e., the probe 103 is attached to the attachment), and a reaction force of the ossicles can be quantitatively measured due to the easy attachment and thus a user-friendly measuring probe can be provided. In addition, since the tip 103b of the probe 103 comes in direct contact with the ossicles 900, the easy attachment enables the probe 103 to be easily replaced and improvement in sanitation to be achieved.

Figure 10:
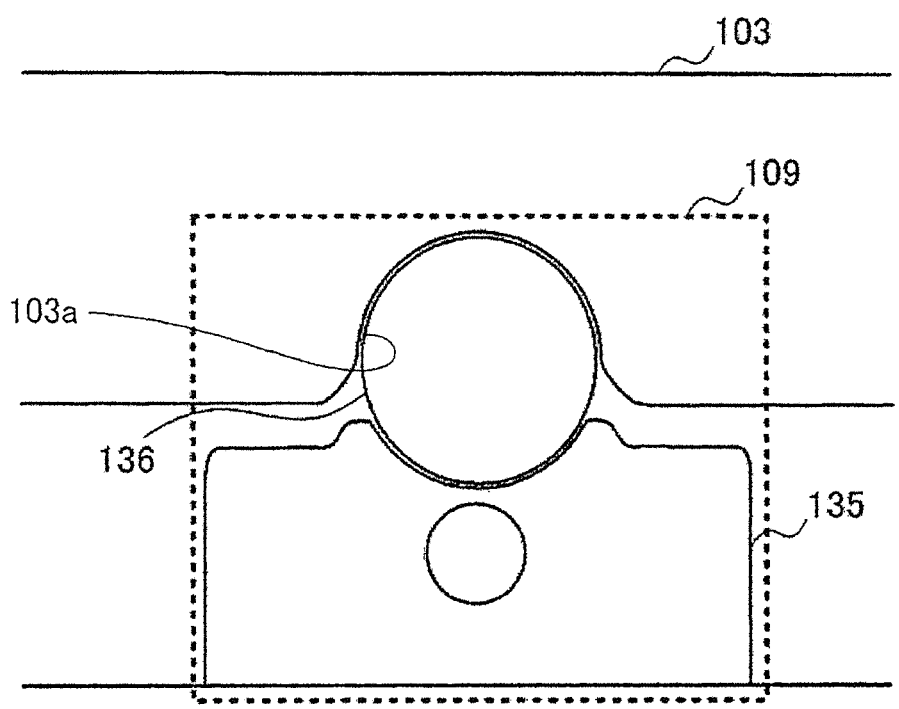
FIG. 10 is a cross sectional view of a probe and a fulcrum metal fitting according to the first example.

In addition, the probe 103 may have a recess 103a formed near the center of gravity as illustrated in FIG. 10. In the example of FIG. 10, the fulcrum metal fitting 109 includes a magnet 136 (a support unit) formed in a spherical shape and a base 135 that supports the magnet 136 in a way that the magnet fits into the base. In addition, the semi-round-shaped recess 103a into which the magnet 136 fits is formed near the center of gravity of the probe 103. With this configuration, the probe 103 can be installed to sit well in the fulcrum metal fitting 109. In addition, since the probe 103 is supported by the spherical magnet 136 coming in contact with a part of an inner surface of the recess 103*a* (point contact), the probe 103 can smoothly move in a rotation direction when the actuator 116 gives rotational vibration thereto. In addition, it is possible for the probe 103 to make it easy to be detached from the measuring probe 100 and attached to the measuring probe 100. In addition, since the probe 103 can be fixed to the fulcrum metal fitting 109 with a magnetic force of the magnet 136, it is possible to prevent the probe 103 from dropping out of the measuring probe 100. In addition, even when the probe 103 is detached from the measuring probe 100 for use, the recess 103*a* serves as a mark for positioning the operator's hand, and thus when the operator holds the probe 103 in his or her hand, he or she can simply identify the position near the center of gravity of the probe 103 without visually checking it, and thus a user-friendly probe can be provided.

The measuring probe 100 may have an elastic body that elastically comes in contact with the probe 103. Any elastic body may be employed as long as it imparts an elastic resistance force to the probe 103 in contact therewith. In this example, when the plate springs 107 are used will be described. The plate springs 107 elastically come in contact with the probe 103 and impart an elastic resistance force thereto. Specifically, the plate springs 107*a* and 107*b* are screwed to the first upper cover 101 by the tapping screws 108*a* and 108*b* as illustrated in FIG. 4, and when the first upper cover 101 is set to the second upper cover B102, the plate springs are attached to the probe 103 in contact therewith. Accordingly, the probe 103 is biased by the magnet 136. With the above-described configuration, an inertial term of the probe 103 can be cancelled, and a reaction force of the ossicles can be accurately measured. In addition, since the plate springs 107 can be replaced if the above-described configuration is employed, a user-friendly measuring probe can be provided.

The fulcrum metal fitting 109 may be pinned and attached to the lower cover A106 with the fulcrum fitting fixing pin 111 as a fixation fulcrum of the probe 103 as illustrated in FIG. 4.

In addition, the fulcrum metal fitting 109 may include the spherically formed magnet 136 and the base 135 that provide a support to fit into the recess 103*a* near the center of gravity of the probe 103 as illustrated in FIG. 10. The magnet 136 attracts the probe using a magnetization force. This disclosure is not limited to this aspect, and a spherically formed support unit may be formed of a non-magnetic material and a magnet separate from the support unit may be provided. In this example, by interposing the support unit between a probe and the magnet the support unit may be attracted to the probe due to a magnetization force of the magnet.

The piezoelectric sensor 117 is disposed to be interposed between the probe 103 and the actuator 116, and measures a reaction force exerted to the actuator 116 by the rotationally vibrating probe 103. The measured reaction force is transmitted to the charge amplifier 112, and the charge amplifier 112 converts the reaction force into a voltage and outputs it. The piezoelectric sensor 117 specifically generates a charge signal when a reaction force to a force exerted by the actuator 116 to the probe 103 is applied thereto via the probe 103. At this time, the charge amplifier 112 converts the generated charge signal into a voltage and outputs it. For the piezoelectric sensor 117, specifically, a piezoelectric sensor (piezo-type piezoelectric ceramics), a multilayer piezoelectric sensor, or the like may be used.

Figure 9:
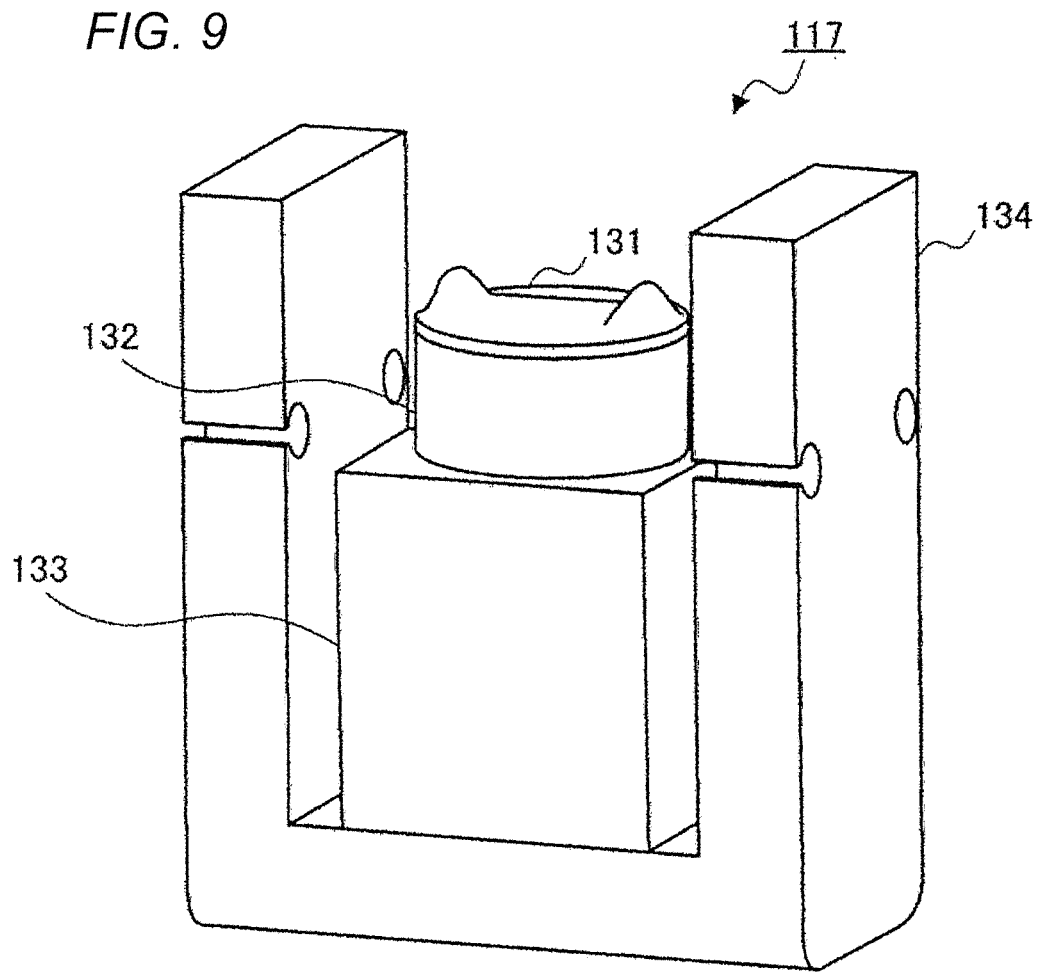
FIG. 9 is a perspective view of a force sensor according to the first example.

In addition, the piezoelectric sensor 117 may support the probe 103 on a plane or a line, rather than a point. An example in which the piezoelectric sensor 117 supports the probe 103 in contact therewith on a line will be described using FIG. 9. The piezoelectric sensor 117 is provided with a lateral vibration prevention mechanism 131, a magnet 132, a sensor body 133, and a sensor holder 134 as illustrated in FIG. 9.

The lateral vibration prevention mechanism 131 is a member that prevents lateral vibration of the probe 103. The lateral vibration prevention mechanism 131 is, for example, a substantially disc-like member, and the upper part thereof may have a concave-shaped probe receiver having both sides with raised heights formed substantially at the center (in other words, a semi-cylindrical protruding part may be formed at the center, and protruding parts that prevent lateral vibration with heights set to higher than the protruding part at the center may be formed at both sides). With this configuration, while the probe is detachably supported with a binding force due to a magnetic force of the magnet 132, the core of the probe 103 can be automatically aligned with the magnet 132 due to the inclined surface of the protruding parts formed at the both sides, and thus lateral vibration of the probe 103 can be prevented. Any material may be used for the lateral vibration prevention mechanism 131 as long as it is light and has rigidity of a certain level and, for example, using stainless steel or the like therefor is considered.

The magnet 132 is a member that attracts the probe 103 to the concave probe receiver of the lateral vibration prevention mechanism 131 using its magnetic force to stably support the probe. Any material may be used for the magnet 132 as long as it can detachably restrain the probe 103 with a magnetic attraction force and, for example, using a neodymium magnet or the like therefor is considered.

The sensor body 133 is the sensor body of the piezoelectric sensor 117. The sensor body 133 has a piezoelectric element having a piezoelectric effect, and converts a force exerted from the probe 103 into a charge signal and outputs it.

The sensor holder 134 is a member of holding (adhering) the sensor body 133. In addition, the sensor holder 134 may have one or more round grooves (four round grooves in the example of FIG. 9) and hold signal lines (codes) from the sensor body 133.

In addition, as an example, the piezoelectric sensor 117 may be configured such that a non-conductive member is interposed between the lateral vibration prevention mechanism 131 and the magnet 132 and the sensor body 133. With this configuration, an insulating region can be provided between the sensor body 133 of the piezoelectric sensor 117 and the probe 103 via the lateral vibration prevention mechanism 131, and since the surrounding of the ossicles 900 is very sensitive to electricity, the probe 103 of the measuring probe 100 can be in contact with the ossicles 900 more safely.

The actuator 116 is housed in the actuator holder 114 as illustrated in FIG. 4 and is screwed and attached to the actuator holder 114 using the standard screws 115. For the actuator 116, specifically, a piezoelectric actuator with a displacement magnification mechanism or the like may be used.

The charge amplifier 112 is screwed and attached to the actuator holder 114 using the tapping screw 108*c*, and the actuator holder 114 is screwed and attached to the lower cover A106 using the tapping screws 108*d*, 108*e*, and 108*f*.

The charge amplifier 112 connects to the codes 113 and 123, and the codes 113 and 123 connect to an external device (the information processing device 300 or the like) passing through the code bush 105. The code bush 105 may be attached to the lower cover A106 using a fixing means, for example, a hexagon nut fixing rib, or the like. By employing the above-described configuration, it is possible to make the attachment of the code bush 105 easy. In addition, the charge amplifier 112 may be configured separately from an OP amplifier unit that is responsible for analog arithmetic operations and amplification and a power supply unit that supplies power to the actuator and, accordingly, the codes 113 and 123 may separately have a line to connect to the OP amplifier unit and output analog signals (signal line) and a line to connect to the power supply unit and supplying power to the actuator 116 (power line). With this configuration, the OP amplifier unit needs to be provided near the piezoelectric sensor 117 to pick up noise. However, if the other part (the power supply unit) is provided outside the measuring probe 100, the measuring probe 100 can be treated as a handpiece and have a more compact size. In addition, with the above-described configuration, it is possible to reduce the influence of inductive noise with respect to an output signal due to the divided signal line and power line.

The measuring probe 100 according to the second structural example is used by attaching the first upper cover 101 to the second upper cover B102, attaching the second upper cover B102 to the lower cover A106, and attaching the locking knob 104 thereto using the E ring 110 for E ring stop. A part of the first upper cover 101 and a part of the second upper cover B102 form a hinge mechanism, and when the first upper cover 101 and the second upper cover B102 pivot around the hinge mechanism in a mutually connected state, the first upper cover 101 can be opened and closed with respect to the second upper cover B102. With the above-described configuration, the plate springs 107a and 107b screwed by the tapping screws 108a and 108b can be replaceable, and thus a user-friendly measuring probe can be provided.

With respect to the measuring probe 100, a vibration exciter is the elongated rod-like probe 103, the probe 103 is supported by the fixation fulcrum and the force sensor at two points near the center of gravity of the probe and the base end 103c, the actuator 116 applies vibration such as rotational vibration having a constant amplitude or the like to the probe 103 with respect to the fulcrum near the center of gravity, the force sensor includes the piezoelectric sensor 117 and the charge amplifier 112, the piezoelectric sensor 117 generates a charge signal when a reaction force to a force exerted by the actuator to the probe 103 is applied thereto via the probe 103, and the charge amplifier 112 converts the generated charge signal into a voltage and outputs it as illustrated in FIG. 4. By employing the above-described configuration, a reaction force of the ossicles 900 can be measured, the degree of improvement in mobility of an ear with ossicular fixing before and after treatment can be evaluated, and improvement in post-surgical consequences and a reduction in risks of revision surgery can be achieved.

The measuring probe 100 according to the second structural example includes the second upper cover B102 and the lower cover A106 formed in a shape for operators' hands when a person grabs the measuring probe 100 in his or her hand as illustrated in FIG. 5 to help them easily grab the second upper cover B102 and the lower cover A106 of the measuring probe 100 when he or she grabs and holds it. By employing the above-described configuration, the measuring probe 100 can be treated as a handpiece, and thus a user-friendly measuring probe 100 can be provided.

Although the locking knob 104 is illustrated as being attached to both sides of the second upper cover B102 in FIG. 5 for the sake of description, the locking knob 104 may be provided on any of the left and right sides so that the knob locks only a single side. Furthermore, when the locking knob 104 is provided only on a single side, an opening/closing knob to open or close the first upper cover 101 upward and downward with respect to the second upper cover B102 with one touch may be provided on the other side.

The measuring probe 100 includes the second upper cover B102 and the lower cover A106 formed in a shape for operators' hands when they grab the measuring probe 100 in their hands as illustrated in FIGS. 6A and 6B to help the operators easily grab the measuring probe 100 when they grab and hold the measuring probe 100. By employing the above-described configuration, the measuring probe 100 can be treated as a handpiece and thus a user-friendly measuring probe 100 can be provided. In addition, although the measuring probe 100 is assumed to be used as a handpiece and sizes of each part (unit: mm) are described in FIG. 6B as examples thereof, sizes of the measuring probe are not limited thereto, and any size may be employed as long as the measuring probe can be easily held in human hands as a handpiece in that size.

In addition, the lower cover A106 may also function as a rigidity/inertial force applying member that applies rigidity with which relative positions of the fulcrum metal fitting 109 (fulcrum) and the actuator 116 can be kept constant and an inertial force with which the measuring probe 100 can resist vibration of the actuator 116 to the measuring probe. By applying rigidity with which relative positions of the fulcrum metal fitting 109 and the actuator 116 can be kept constant and an inertial force with which the measuring probe can resist vibration of the actuator 116 to the measuring probe 100, the vibration of the lower cover A106 and the second upper cover B102 and shake of the measuring probe 100 caused by the reaction to the vibration of the actuator 116 can be suppressed, and detection accuracy of the piezoelectric sensor 117 can be improved.

As a method of causing the lower cover A106 to function as a rigidity/inertial force applying member, a method of forming the lower cover A106 of a material having a higher rigidity and specific gravity than the second upper cover B102 can be exemplified. In addition, instead of causing the lower cover A106 to function as a rigidity/inertial force applying member, for example, a metallic rigidity/inertial force applying member may be attached to the bottom of the lower cover A106, or the frame of the attachment 120 may be made as a metallic rigidity/inertial force applying member. In any of the configurations, the relative positions of the fulcrum metal fitting 109 and the actuator 116 can be kept constant and an inertial force with which the measuring probe 100 can resist vibration of the actuator 116 is applied to the measuring probe, and therefore detection accuracy of the piezoelectric sensor 117 can be improved.

In addition, the lower cover A106 may function as a center of gravity positioning member that positions the center of gravity of the measuring probe 100 to the tip 103b side of the probe 103 rather than at the fulcrum near the center of gravity of the probe 103. By positioning the center of gravity of the measuring probe 100 to the tip 103b side of the probe 103 rather than at the fulcrum near the center of gravity of the probe 103, vibration of the lower cover A106 and the second upper cover B102 caused by the reaction to vibration of the actuator 116 can be suppressed, and detection accuracy of the piezoelectric sensor 117 can be improved.

As a method of causing the lower cover A106 to function as a center of gravity positioning member, a method of forming the lower cover A106 of a material having a higher specific gravity than the second upper cover B102 and choosing a thickness of the lower cover A106 or the like so that the center of gravity of the lower cover A106 is positioned on the tip 103b side of the probe 103 rather than at the fulcrum near the center of gravity of the probe 103. In addition, instead of causing the lower cover A106 to function as a center of gravity positioning member, for example, a metallic center of gravity positioning member may be attached to the bottom of the lower cover A106, or the frame of the attachment 120 may be made as a metallic center of gravity positioning member. In any of the configurations, the center of gravity of the measuring probe 100 is positioned on the tip 103b side of the probe 103 rather than at the fulcrum near the center of gravity of the probe 103, thereby vibration of the lower cover A106 and the second upper cover B102 can be suppressed, and therefore detection accuracy of the piezoelectric sensor 117 can be improved.

Figure 7:
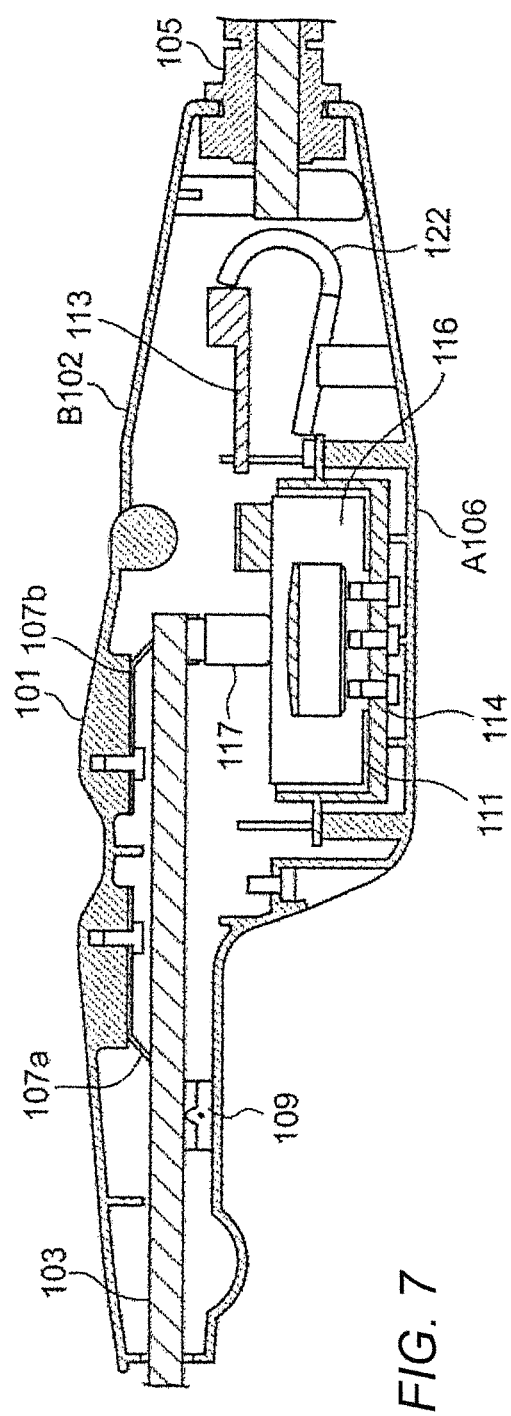
FIG. 7 is a cross sectional view of the measuring probe illustrated in FIG. 4.

The plate springs 107a and 107b are in contact with the probe 103 from above as illustrated in FIG. 7. In addition, the probe 103 is supported by and attached to the two points that are the fulcrum metal fitting 109 positioned near the center of gravity of the probe 103 and the piezoelectric sensor 117 such that the probe is supported by the two points that are near the center of gravity and the base end 103c. With this configuration, the actuator 116 can apply vibration such as rotational vibration having a constant amplitude or the like with respect to the fulcrum near the center of gravity to the probe 103 via the piezoelectric sensor 117.

Process Executed by Middle Ear Sound Transmission Characteristics Evaluation System 1

Figure 8:
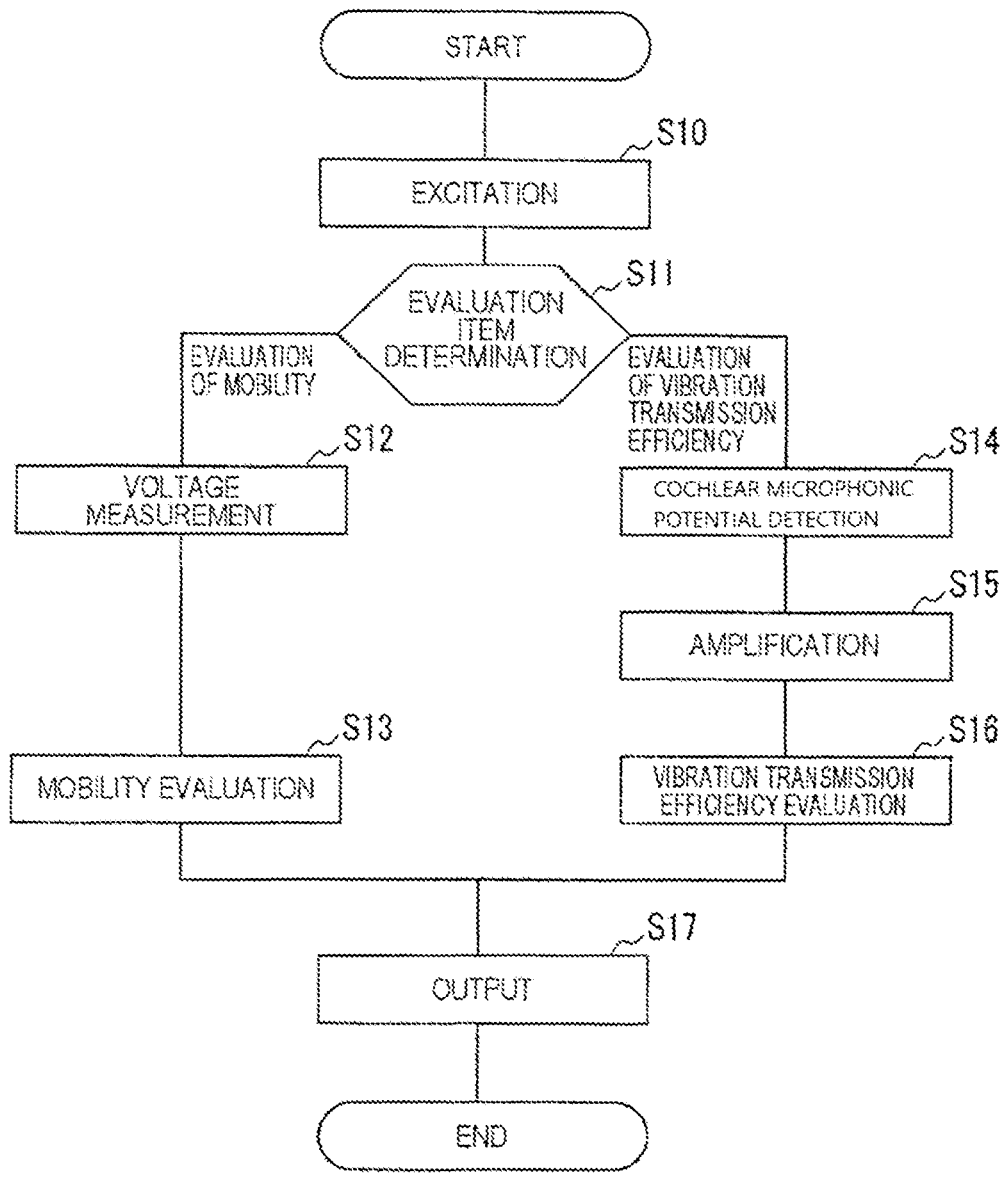
FIG. 8 is a flowchart showing a process executed by the middle ear sound transmission characteristics evaluation system according to the first example.

An example of a process executed by the middle ear sound transmission characteristics evaluation system 1 will be described with reference to the flowchart of FIG. 8.

The middle ear sound transmission characteristics evaluation system 1 executes a series of processes including an excitation step S10, an evaluation item determination step S11, a voltage measurement step S12, a mobility evaluation step S13, a cochlear microphonic potential detection step S14, an amplification step S15, a vibration transmission efficiency evaluation step S16, and an output step S17.

The excitation step S10 is a processing step in which vibration is applied to the ossicles 900 by bringing the tip 103b of the probe 103 that has been vibrated by the actuator 116 in contact with the ossicles 900. The excitation step S10 continues until the end of the voltage measurement step S12 and the cochlear microphonic potential detection step S14.

The evaluation item determination step S11 is a processing step in which whether to evaluate mobility or vibration transmission efficiency is determined. If it is determined to "evaluate mobility," the processes from the voltage measurement step S12 are executed.

The voltage measurement step S12 is a processing step in which a voltage in accordance with a reaction force from the probe 103 to the actuator 116 is measured and output when vibration is applied to the ossicles 900 in the excitation step S10.

The mobility evaluation step S13 is a processing step in which the mobility of the ossicles 900 is categorized to any of a plurality of mobility evaluation levels on the basis of the voltage measured by the voltage measurement step S12.

The output step S17 is a processing step in which the value of the mobility evaluation level and the value of the vibration transmission efficiency evaluation level are output. In this example, in the output step S17, a process of outputting the value of the mobility evaluation level categorized in the mobility evaluation step S13 is executed.

Meanwhile, if it is determined to "evaluate vibration transmission efficiency," the processes from the cochlear microphonic potential detection step S14 are executed in the evaluation item determination step S11.

The cochlear microphonic potential detection step S14 is a processing step in which the electrode 600 is installed at the round window or near the round window and a cochlear microphonic potential generated when vibration is applied to the ossicles 900 in the excitation step S10 is detected.

The amplification step S15 is a processing step in which the cochlear microphonic potential detected in the cochlear microphonic potential detection step S14 is amplified.

The vibration transmission efficiency evaluation step S16 is a processing step in which the vibration transmission efficiency of the ossicles 900 is categorized into any of a plurality of vibration transmission efficiency evaluation levels on the basis of the cochlear microphonic potential amplified in the amplification step S15.

In the output step S17, a process of outputting the value of the vibration transmission efficiency evaluation level categorized in the vibration transmission efficiency evaluation step S16 is executed.

Since the mobility and vibration transmission efficiency of the ossicles 900 can be quantitatively evaluated during middle ear surgery using the probe 103 by executing the above-described series of processes, the middle ear surgery can be performed while quantitatively determining the degree of hearing restoration.

The above-described example merely describes the principle and desired effects, and does not limit this disclosure. Those skilled in the technology can make addition or modification with respect to the example on the premise that it does not depart from the scope of the disclosure. That is, any equivalent addition or modification made by those skilled in the art on the premise that it does not depart from the technical philosophy belongs to the appended claims.

Although, for example, when there are five mobility evaluation levels and vibration transmission efficiency evaluation levels, respectively, "1" to "5" has been exemplified in the above-described example, each of the number of levels may be four or smaller, or 6 or more. In addition, there is no need to make the number of mobility evaluation levels the same as the number of vibration transmission efficiency evaluation levels.

In addition, although FFT analysis is exemplified as frequency analysis executed by the mobility evaluation unit 331 and the vibration transmission efficiency evaluation unit 332 in the above-described example, the specific frequency component value may be obtained by executing another kind of frequency analysis. The other type of frequency analysis includes a wavelet transform.

In addition, although the magnet 136 is formed in a spherical shape and the magnet 136 is in point contact with an inner surface of the recess 103a in the above-described example, a shape of the magnet 136 is not limited to a spherical shape and may be any shape in which it can be in partial contact with an inner surface of the recess 103a. For example, the magnet 136 in a cone shape such as a conical shape or a pyramid shape can also be employed. In addition, a contact mode of the magnet 136 with respect to an inner surface of the recess 103a is not limited to point contact, and a line contact or a surface contact is possible.

A modified example of the fulcrum metal fitting 109 will be described using FIGS. 11A and 11B. FIG. 11A is a perspective view of a state in which the probe 103 is removed and FIG. 11B is a cross sectional view of a state in which the probe 103 is attached according to a modified example of the fulcrum metal fitting 109. In the fulcrum metal fitting 109B, the magnet 136B is built in a recess 137 provided on the bottom surface of a base 135B of the fulcrum metal fitting 109B.

In addition, the recess 103a of the probe 103 has a triangular shape when viewed in a longitudinal section in the direction in which the probe 103 extends. On the bottom surface among inner surfaces of the base 136B of the fulcrum metal fitting 109 on which the probe 103 is placed, a supporting protrusion 138 formed in a triangular shape when viewed in a longitudinal section in the direction in which the probe 103 extends is formed. The supporting protrusion 138 comes in line contact with the recess 103a.

In addition, in this modified example, a sliding surface 139 formed of a Teflon resin is formed on a side surface among inner surfaces of the base 136B of the fulcrum metal fitting 109B that is in contact with the probe 103. Since the probe 103 vibrates in contact with the sliding surface 139 as described above, measurement can be performed with good accuracy with smooth operations of the probe 103.

Second Example

A second example will be described below with reference to the drawings.

In the following description, the same reference numerals will be given to the same configurations as those of the first example, and description thereof will be omitted. In addition, description with respect to the same actions and effects as those of the first example will also be omitted.

Configuration of Middle Ear Sound Transmission Characteristics Evaluation System 2

Figure 13:
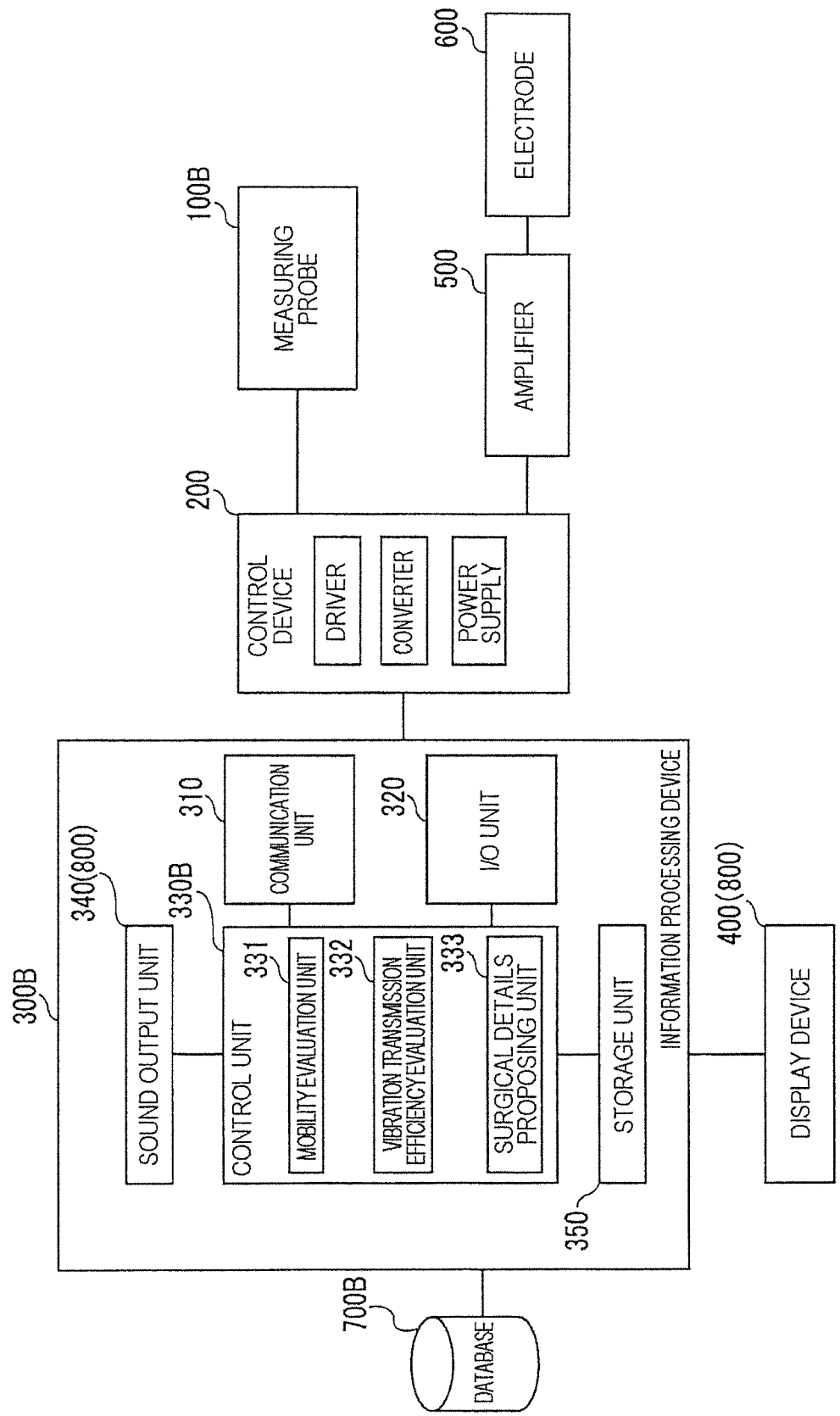
FIG. 13 is a block diagram illustrating a functional configuration of the middle ear sound transmission characteristics evaluation system according to the second example.

FIG. 12 is a system diagram illustrating an example of a configuration of a middle ear sound transmission characteristics evaluation system 2, and FIG. 13 is a block diagram illustrating a functional configuration of the middle ear sound transmission characteristics evaluation system 2.

The middle ear sound transmission characteristics evaluation system 2 further has a function of accumulating measured data and proposing selected surgical details on the basis of the stored data, unlike the above-described middle ear sound transmission characteristics evaluation system 1. In addition, a measuring probe 100B has further improved rigidity, cleanness, waterproof than the above-described measuring probe 100. These points will be described below.

The middle ear sound transmission characteristics evaluation system 2 includes a control device 200 that controls the measuring probe 100B as illustrated in FIG. 12 and FIG. 13. The control device 200 includes a power supply, a converter, and a driver. In addition, a potential value of a cochlear microphonic connected to an amplifier 500, the potential of which has been amplified by an amplifier, is transmitted to an information processing device 300B via the control device 200.

In addition, a database 700B of this example stores sensor voltage values output by a force sensor before, during, and after surgical treatment, potential values detected from the electrode 600, and treatment details.

Figure 14:
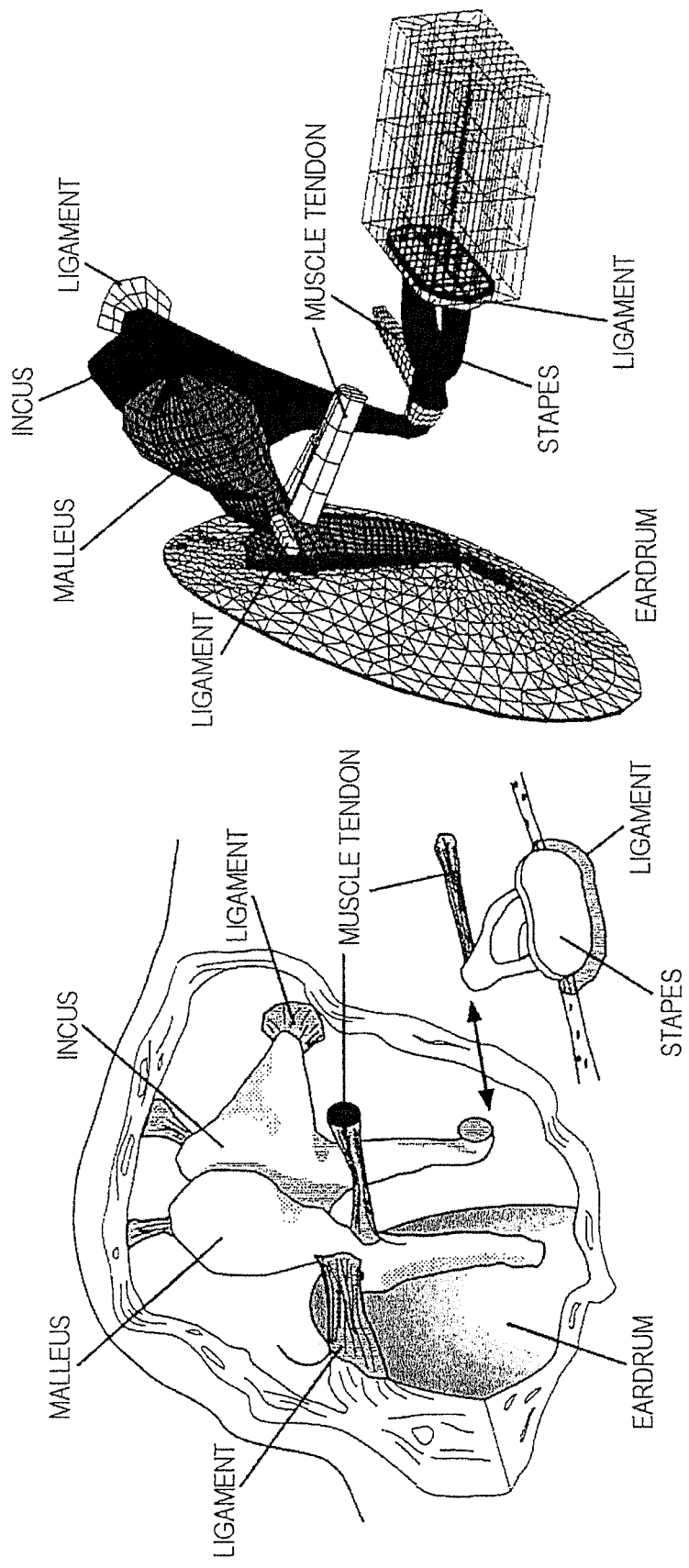
FIG. 14 is a diagram for describing a model of an analysis simulation.

In addition, the database 700B stores assumed symptoms of the ossicles and mobility analysis values calculated in numerical simulations as values of the mobility at the times of the symptoms. Details of a numerical simulation will be described with reference to FIG. 14. FIG. 14 is a diagram for describing a model of an analysis simulation.

In the middle ear sound transmission characteristics evaluation system of this example, numerical simulations using finite element method analysis (FEM analysis) are performed, and analysis values obtained from the analysis are stored in the database 700B as illustrated in FIG. 14.

In the finite element method analysis, the structure of the middle ear shown on the left side of FIG. 14 is reproduced in a 3D model, and it is divided into finite and tiny volume elements. Then, equations of motions established with respect to each of the volume elements when an external force is applied to a part of the 3D model are solved. Accordingly, the displacement amounts of each of the volume elements are analyzed, and thus behavior of the entire 3D model can be evaluated.

Then, symptoms caused by induration or fixing that may appear in the three bones of the ossicles are assumed, and the mobility in each case of the symptoms is analyzed. The mobility can also be evaluated using formula (1). Accordingly, a mobility analysis value corresponding to each assumed symptoms can be calculated.

In addition, a control unit 330B of the information processing device 300B of this example includes a surgical details proposing unit 333 that proposes the selected surgical details to a surgeon.

The surgical details proposing unit 333 proposes the desired surgical details on the basis of at least one of sensor voltage values and potential values measured before, during, and after treatment with reference to sensor voltage values, potential values, and details of surgery stored in the database 700B. The surgical details refer to a site of the middle ear of a patient for which treatment is performed during surgery and details of the treatment.

The surgical details proposing unit 333 may only use a voltage value or a potential value measured before treatment. By using a value after treatment, the degree of restoration can be checked and the reasonability of the treatment method of the surgery can be evaluated.

In other words, a surgical details proposing model is generated in the database 700B.

In a surgical details proposing model, for example, mobility presumed from a sensor voltage value measured before treatment and the details of the surgery actually performed at that time are described as past experience.

Thus, when surgery is to be performed, the current mobility of the ossicles of the patient is presumed from the measured sensor voltage value, the details of the surgery that was actually performed for a similar symptom are checked, and thereby the site of the middle ear of the patient for which treatment is to be performed and the details of the treatment can be determined.

In addition, in the surgical details proposing model, mobility presumed from sensor voltage values measured during and after treatment and the details of the surgery that was actually performed at those times may be described as past experience.

As a method of evaluating the similarity of newly measured data to stored data, it may be evaluated simply by comparing the absolute values of sensor voltage values or the shapes of voltage waveforms.

In addition, in the surgical details proposing model, vibration transmission efficiency presumed from the difference in potentials of the cochlear microphonic detected before treatment and the details of the surgery that was actually performed at that time are described as a past record.

Thus, when surgery is to be performed, the current vibration transmission efficiency of the patient is presumed from the difference in detected potentials of the cochlear microphonic, the details of the surgery that was actually performed for a similar symptom is checked, and thereby the site of the middle ear of the patient for which treatment is to be performed and the details of the treatment can be determined. In addition, in the surgical details proposing model, vibration transmission efficiency presumed from potential values of the cochlear microphonic measured during and after treatment and the details of the surgery that was actually performed at those times may be described as a past record.

As a method of evaluating the similarity of newly measured data to stored data, it may be evaluated simply by comparing the absolute values of potential values of the cochlear microphonic or the shapes of voltage waveforms.

In addition, the surgical details proposing unit 333 proposes the selected surgical details on the basis of the sensor voltage value measured before the surgery with reference to a possible symptom stored in the database 700B and a mobility analysis value.

In other words, by describing mobility analysis obtained from a numerical simulation in the surgical details proposing model, for example, it is possible to determine that the symptom of the ossicles assumed in the numerical simulation is close to the symptom of the patient when the mobility of the ossicles presumed from the sensor voltage value measured before the treatment is similar to the mobility analysis value. In this way, even there is a small amount of past surgical experience, reasonable decision can be made for proper surgical details.

As a method of evaluating the similarity of newly measured data to stored data, it may be evaluated simply by comparing the absolute values or the shapes of voltage waveforms thereof.

Next, a third structural example of the measuring probe 100B will be described with reference to FIGS. 15 to 21. In the following description, the same reference numerals will be given to the same configurations as those of the second structural example, and description will be provided only for different configurations.

In addition, in the following description, the direction in which the probe 103 extends will be referred to as the front-rear direction for the sake of convenience. In addition, the direction orthogonal to the front-rear direction in a plan view (top view) of the probe 103 from the upper cover side will be referred to as the left-right direction.

Figure 15:
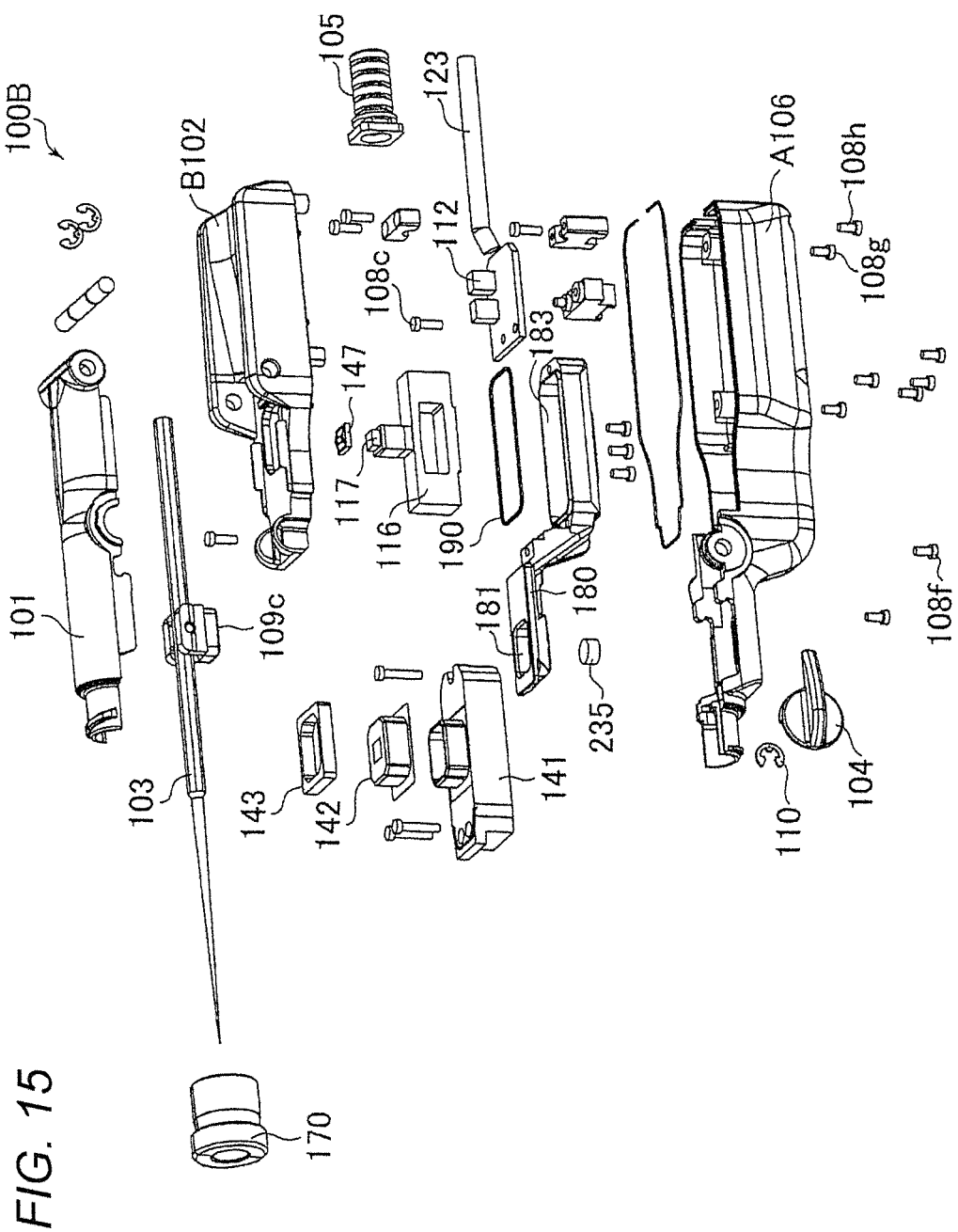
FIG. 15 is an exploded perspective view of a third structural example of the measuring probe.
Figure 16:
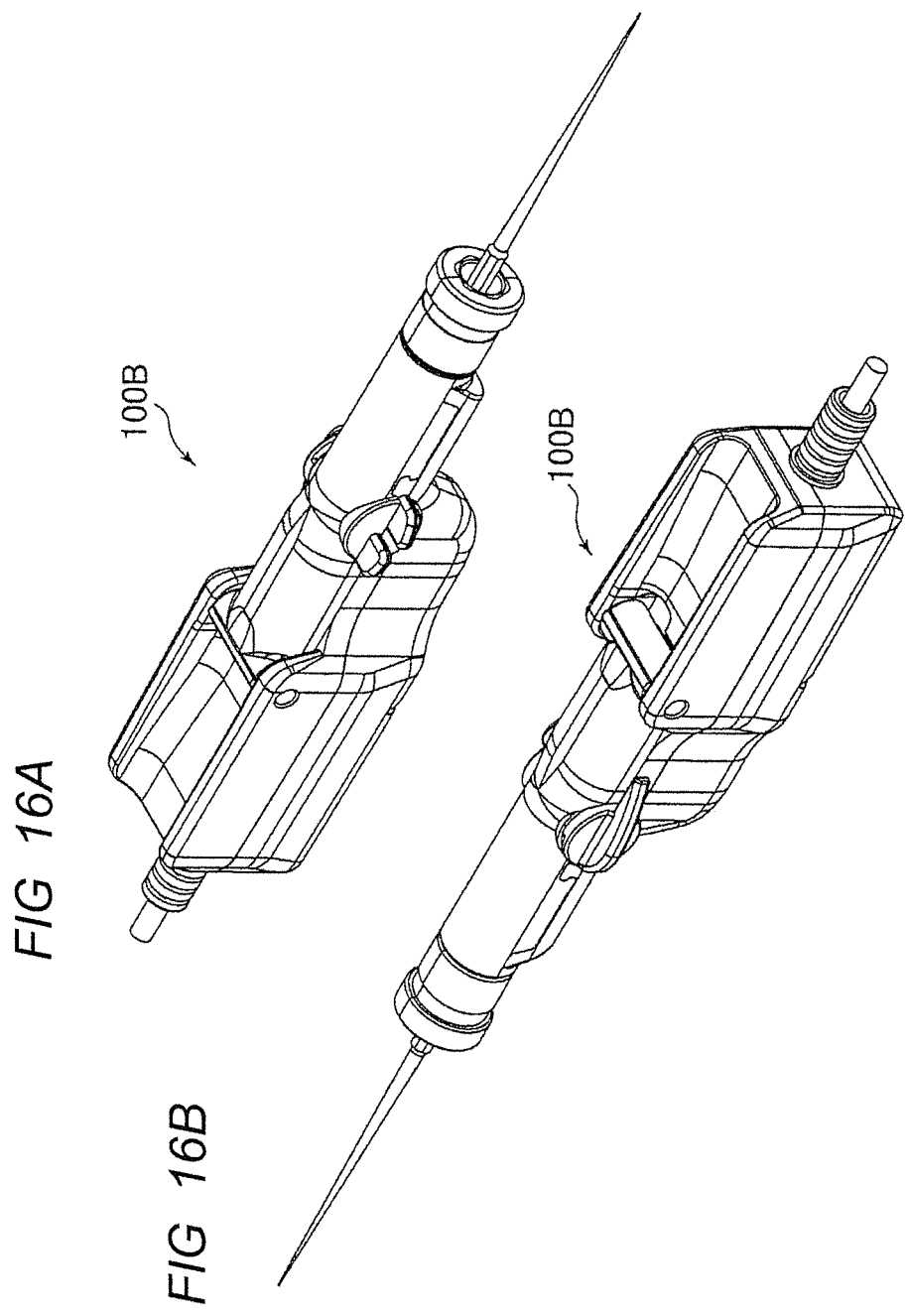
FIGS. 16A and 16B are perspective views of the measuring probe illustrated in FIG. 15.
Figure 17:
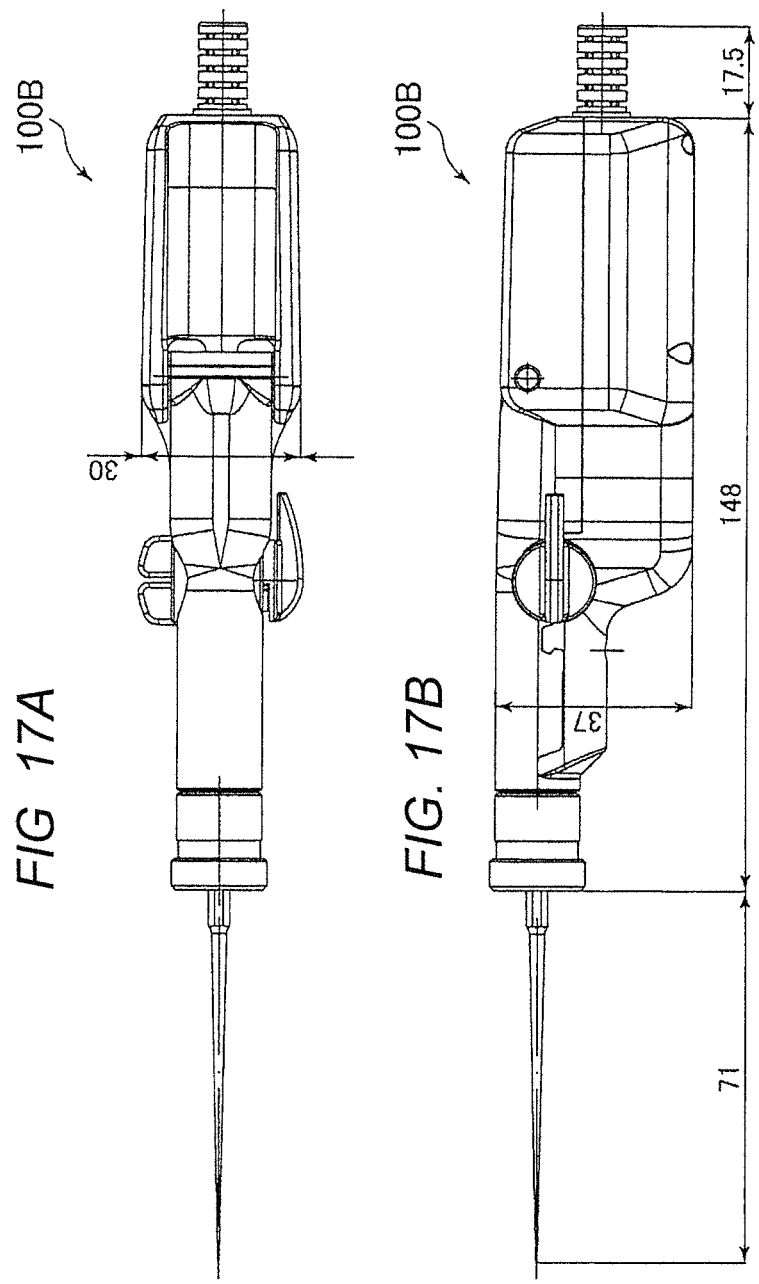
FIG. 17A is a plan view of the measuring probe illustrated in FIG. 16.
FIG. 17B is a side view of the measuring probe illustrated in FIG. 16.
Figure 18:
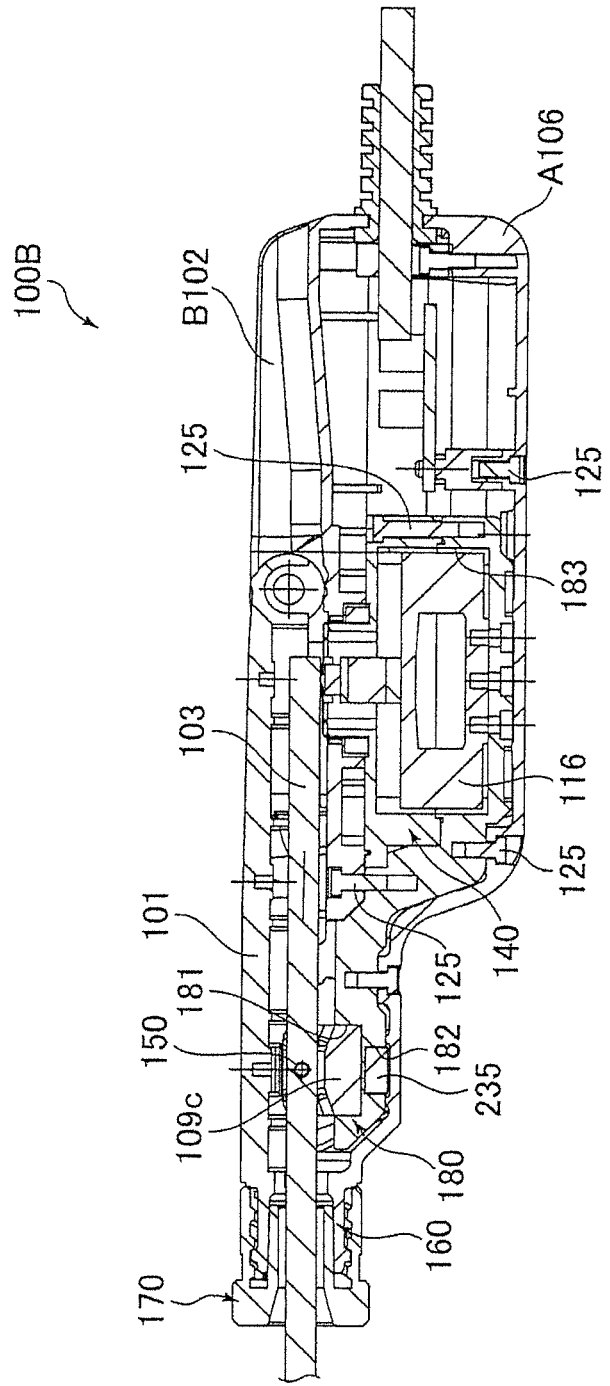
FIG. 18 is a cross sectional view of the measuring probe illustrated in FIG. 17B.
Figure 19:
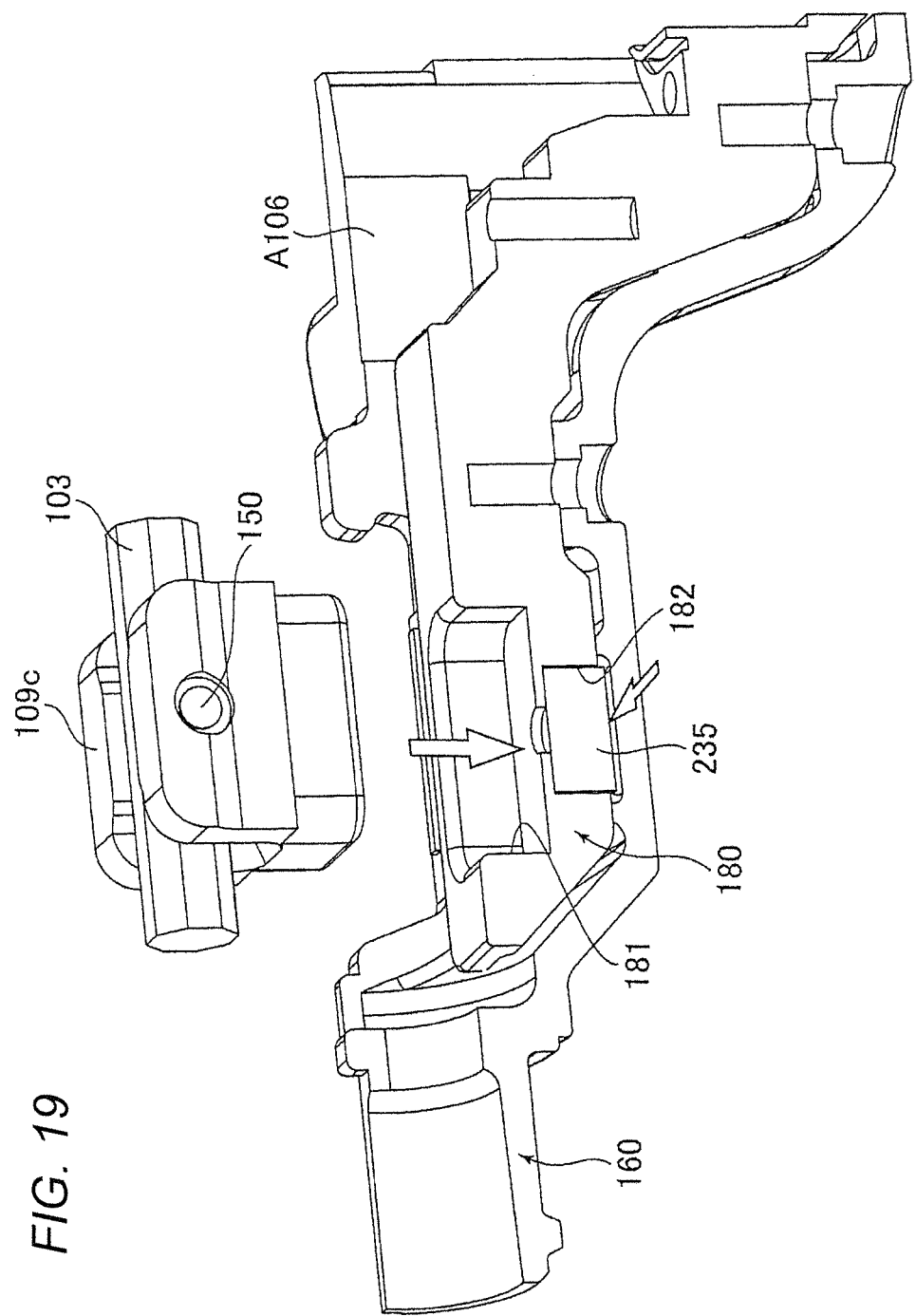
FIG. 19 is an enlarged perspective view illustrating a configuration of a part around a fulcrum metal fitting illustrated in FIG. 18.
Figure 20:
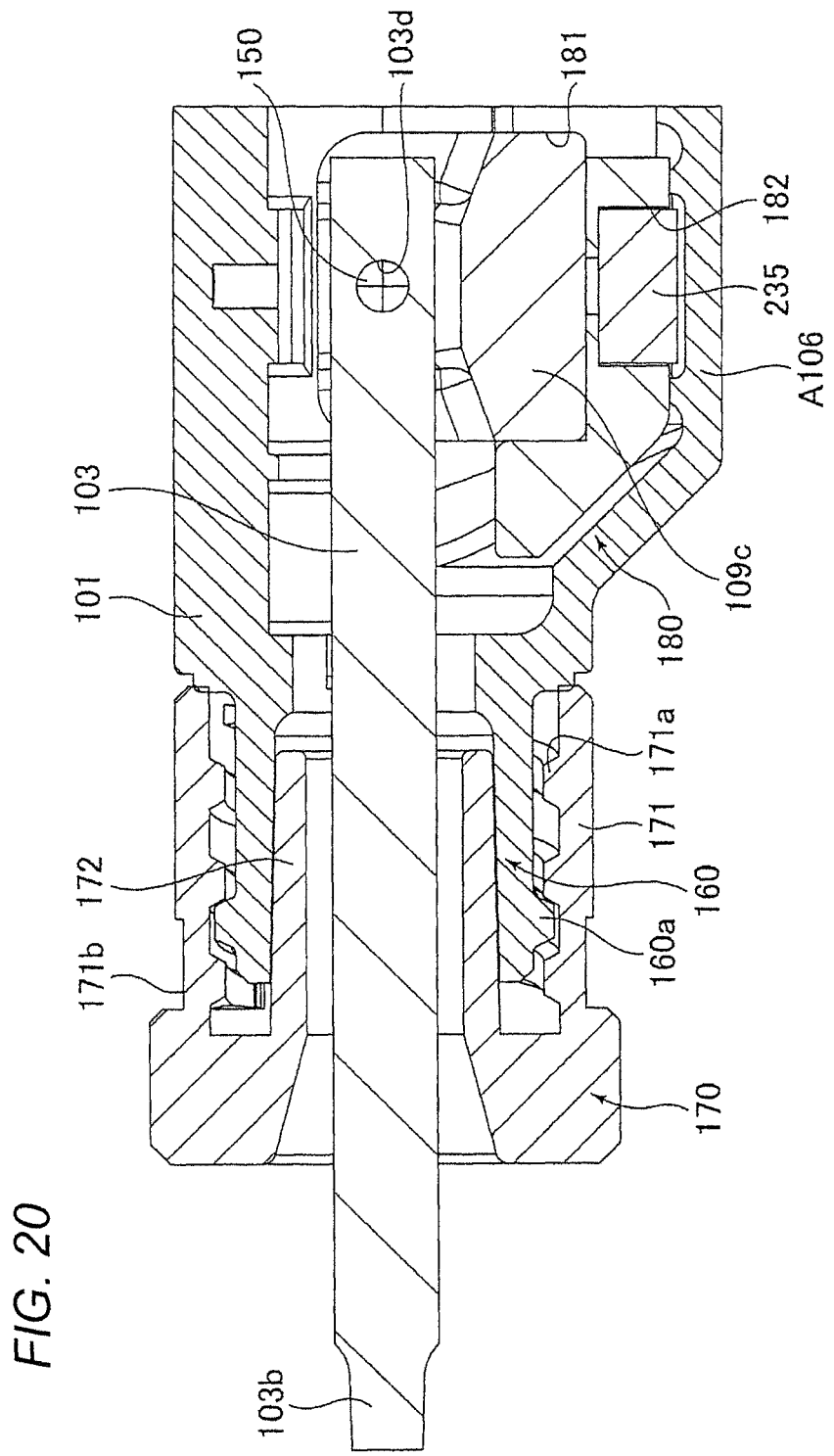
FIG. 20 is a cross sectional view of a periphery of the tip illustrated in FIG. 18.
Figure 21:
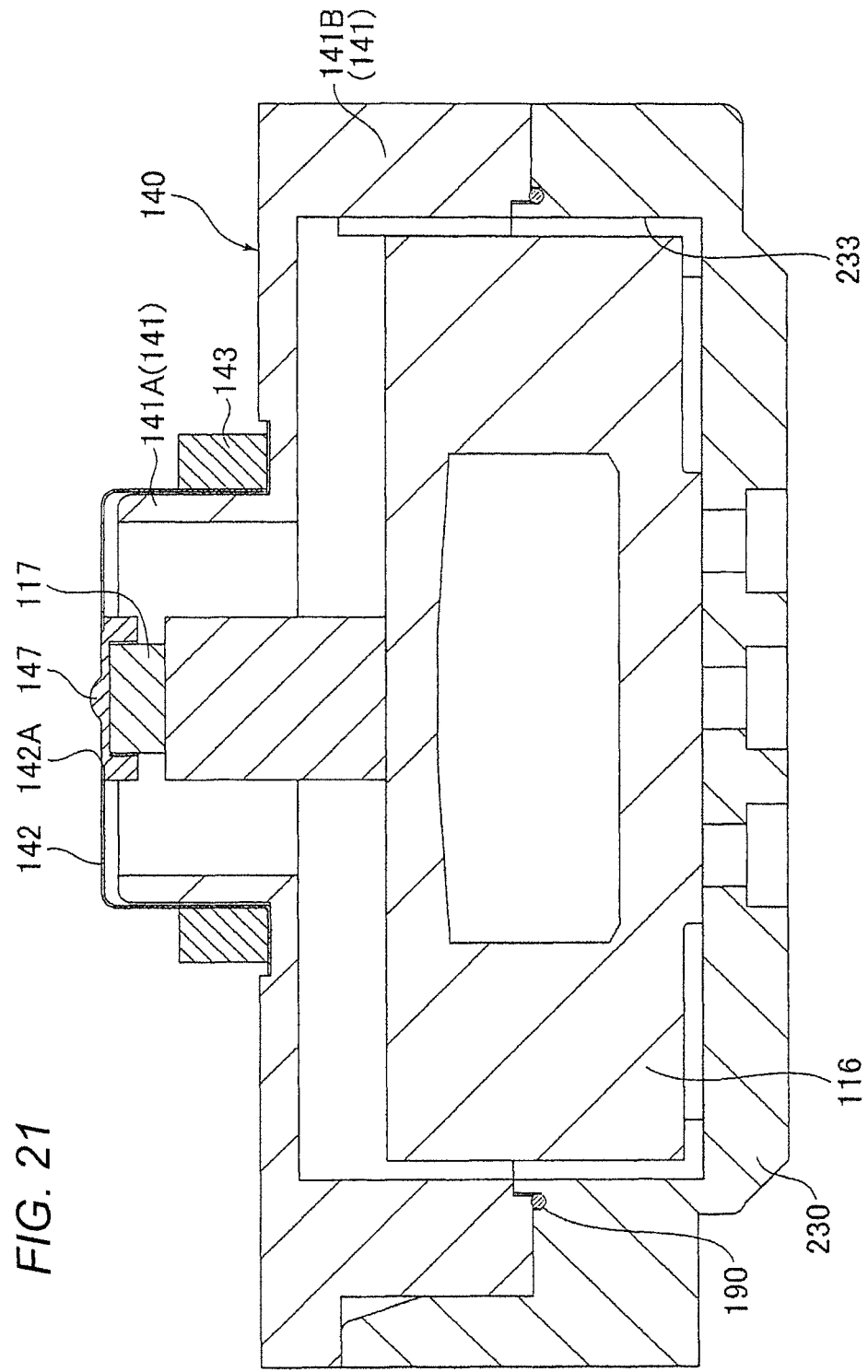
FIG. 21 is a cross sectional view of a periphery of the actuator case illustrated in FIG. 18.

FIG. 15 is an exploded perspective view of a third structural example of the measuring probe 100B. FIG. 16 is a perspective view of the measuring probe 100B. FIG. 17A is a plan view of the measuring probe 100B. FIG. 17B is a side view of the measuring probe 100B. FIG. 18 is a longitudinal sectional view of the measuring probe 100B. FIG. 19 is an enlarged perspective view illustrating a periphery of a fulcrum metal fitting. FIG. 20 is a cross sectional view of a periphery of a tip. FIG. 21 is a cross sectional view of a periphery of an actuator case.

As illustrated in FIGS. 15 to 17A and 17B, the measuring probe 100B according to the third structural example has a similar appearance to the measuring probe 100 according to the second structural example.

The measuring probe 100B includes a metal frame 180 provided with a first housing recess 181 in which a fulcrum metal fitting 109C is housed with the probe 103 supported as illustrated in FIG. 15.

The metal frame 180 has the shape along the lower cover A106 in a side view and extends in the front-rear direction. The metal frame 180 is fixed to the lower cover A106 by a fixing screw 125 housed inside the lower cover A106.

Three housing recesses are formed in the metal frame 180 as illustrated in FIG. 18. The first housing recess 181 receding downward is formed on the front top surface of the metal frame 180.

The first housing recess 181 houses the fulcrum metal fitting 109C. The first housing recess 181 has a rectangular shape having the same size as the fulcrum metal fitting 109C in a top view.

In addition, a second housing recess 182 receding upward is formed on the front lower surface of the metal frame 180.

The second housing recess 182 houses a fixing magnet 235 that fixes the fulcrum metal fitting 109C. That is, the fixing magnet 235 is built into the metal frame 180.

The fixing magnet 235 has a cylindrical shape. The second housing recess 182 has a circular shape having the same size as the fixing magnet 235 in the bottom view.

In addition, the third housing recess 183 receding downward is formed on the rear top surface of the metal frame 180.

The third housing recess 183 houses the actuator 116, the piezoelectric sensor 117, and an actuator case 140.

The actuator case 140 is fixed to the metal frame 180 using the fixing screw 125. In addition, the front side of the second upper cover B102 is fixed to the metal frame 180 using the fixing screw 125.

The fulcrum metal fitting 109C of the measuring probe 100B is formed to cover the probe 103 from both sides in the left-right direction.

In addition, the fulcrum metal fitting 109C includes a rotational shaft 150 that extends orthogonal to the probe 103 in a top view and pivotably supports the probe 103 in the top-bottom direction.

The rotational shaft 150 is fixed to the fulcrum metal fitting 109C through welding in a state in which the rotational shaft rotatably supports the probe 103 as illustrated in FIG. 19. That is, the rotational shaft 150 is disposed as if it penetrates the probe 103 and the fulcrum metal fitting 109C.

The rotational shaft 150 is inserted into an insertion hole 103d of the probe 103 (see FIG. 20) with clearance.

The measuring probe 100B includes a cover constituted by the first upper cover 101, the second upper cover B102, and the lower cover A106 each of which is formed of a synthetic resin material as illustrated in FIG. 18.

The cover has an opening 160 that is formed of the first upper cover 101 and the lower cover A106.

The opening 160 is formed to allow the tip 103b of the probe 103 to protrude outward as illustrated in FIG. 20.

In addition, the measuring probe 100B includes a metal cap 170. The metal cap 170 has a pipe shape that is coaxial with the opening 160 of the cover and is detachably attached to the opening 160.

The metal cap 170 has a double pipe structure in which two pipes are coaxially arranged as illustrated in FIG. 20. That is, the metal cap 170 includes an outer pipe 171 disposed outside in the radial direction and an inner pipe 172 disposed inside the outer pipe 171.

The front opening ends of the respective outer pipe 171 and the inner pipe 172 are connected to each other.

A female screw 171a is formed on the inner circumferential surface of the outer pipe 171. An outer circumferential recess 171b receding inward in the radial direction is formed on the outer circumferential surface of the outer pipe 171.

The opening 160 formed by the first upper cover 101 and the lower cover A106 has a pipe shape and a male screw 160a is formed on the outer circumferential surfaces of the covers. The opening 160 has a reduced diameter than a part positioned on the rear side of the opening 160.

In addition, the metal cap 170 is attached to the cover when the female screw 171a of the outer pipe 171 is mounted to the male screw 160a of the opening 160.

At that time, for example, the entire cover is covered by a sterilizing sheet, an end of the sterilizing sheet (not illustrated) is bound to the outer circumferential recess 171b of the outer pipe 171 using a wound tape, and thus the sterilizing sheet can be fixed to the cover. The entire measuring probe 100B can be kept clean by having the metal cap 170 subject to heat treatment separately.

The outer circumferential surface of the outer pipe 171 of the metal cap 170 and a part of the cover positioned at the rear side of the opening 160 form one surface in the radial direction.

The inner pipe 172 of the metal cap 170 is inserted into the opening 160. The probe 103 is inserted into the inner pipe 172.

In addition, the measuring probe 100B includes the actuator case 140 covering the actuator 116 as illustrated in FIG. 21. The inside of the actuator case 140 has a watertight structure.

The actuator case 140 includes a case body 141 that opens in the top-bottom direction, a waterproof sheet 142 that coats the upper side of the case body 141, and a sheet fixing frame 143 that fixes the waterproof sheet 142 to the case body 141.

The case body 141 is formed in a two-step square pipe shape. The case body 141 includes an upper pipe positioned on the upper side and a lower pipe positioned on the lower side. The upper pipe and the lower pipe are formed to be integrated and coaxially disposed.

The case body 141 has a rectangular shape that is longer in the front-rear direction than in the left-right direction in a top view. The upper pipe 141A of the case body 141 is smaller than the lower pipe 141B in the front-rear direction. The upper pipe 141A is disposed at the center of the upper surface of the lower pipe 141B in the front-rear direction.

An internal structure of the actuator case 140 will be described.

In a state in which the actuator 116 and the piezoelectric sensor 117 are housed in the third housing recess 183 of the metal frame 180, the metal frame 180 is placed in the case body 141. A waterproof O ring 190 is disposed between the metal frame 180 and the case body 141.

The waterproof sheet 142 is formed in a pipe shape having an apex, and the lower end protrudes outward in the radial direction. A communication hole 142A is formed at the apex of the waterproof sheet 142.

The waterproof sheet 142 coats the entire upper pipe 141A of the case body 141, and the lower end thereof is in contact with the upper surface of the lower pipe 141B.

The sheet fixing frame 143 is disposed at the part on the upper surface of the lower pipe 141B outside the upper pipe 141A in a top view.

The sheet fixing frame 143 has a rectangular shape in a top view. The lower end of the waterproof sheet 142 is sandwiched by and fixed to the sheet fixing frame 143 and the upper surface of the lower pipe 141B of the case body 141. The sheet fixing frame 143 adheres to the upper surface of the lower pipe 141B with an adhesive.

In this example, a probe holding metal fitting 147 is disposed on the piezoelectric sensor 117. The probe holding metal fitting 147 is disposed into the communication hole 142A of the waterproof sheet 142 and comes in contact with a space on an upper side of the waterproof sheet 142.

The probe holding metal fitting 147 adheres to the lower surface of the apex of the waterproof sheet 142 with an adhesive. As described above, by disposing an O ring or adhesive on the border lines between each component and another component constituting the actuator case 140, the inside of the actuator case 140 has a watertight structure, and thus the measuring probe 100B has a waterproof property.

Process Executed by Middle Ear Sound Transmission Characteristics Evaluation System 2

Figure 22:
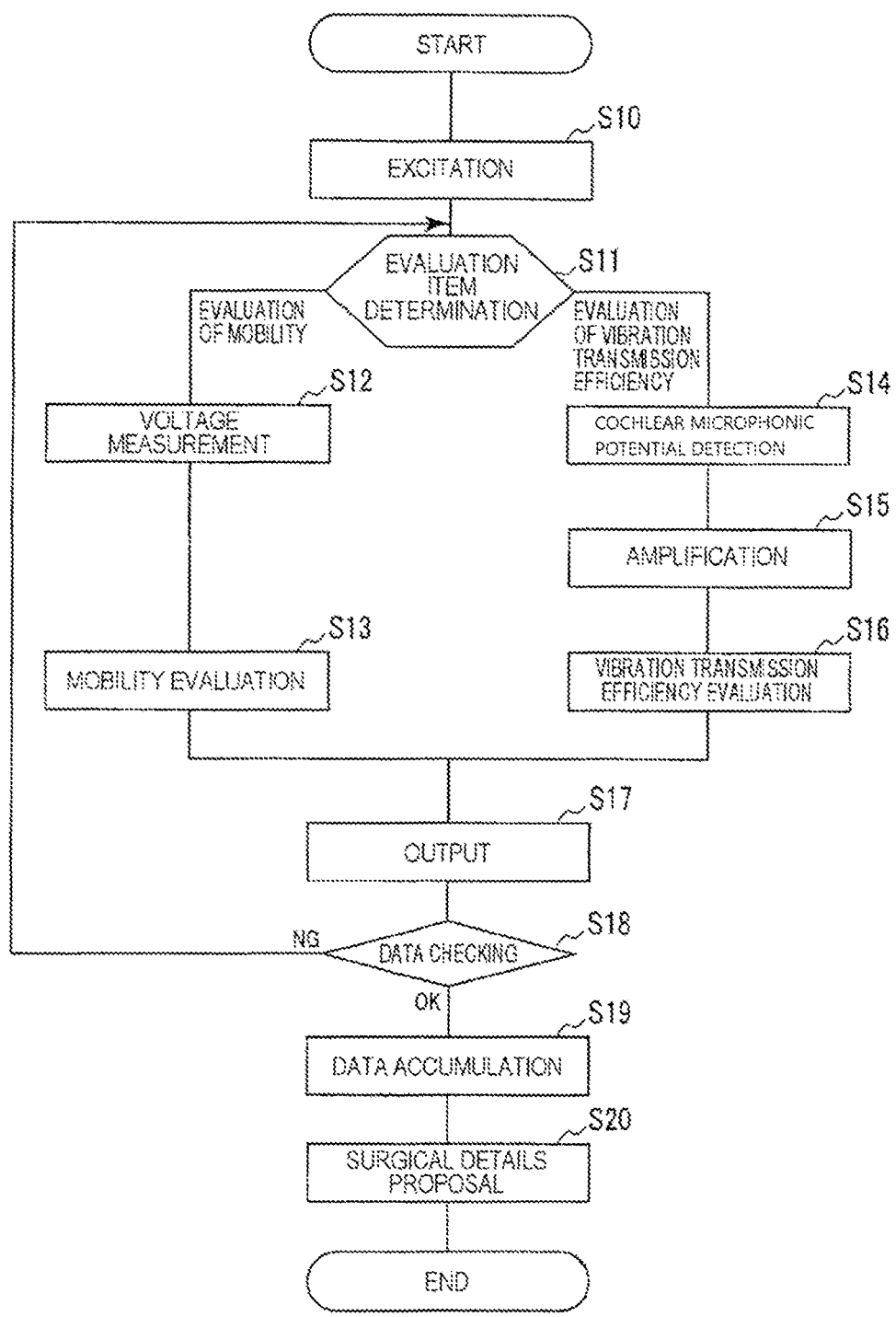
FIG. 22 is a flowchart showing a process executed by the middle ear sound transmission characteristics evaluation system according to the second example.

Next, a series of processes executed by the middle ear sound transmission characteristics evaluation system 2 of this example will be described with reference to the flowchart of FIG. 22.

The middle ear sound transmission characteristics evaluation system 2 executes a series of processes including an excitation step S10, an evaluation item determination step S11, a voltage measurement step S12, a mobility evaluation step S13, a cochlear microphonic potential detection step S14, an amplification step S15, a vibration transmission efficiency evaluation step S16, an output step S17, a data checking step S18, a data accumulation step S19, and a surgical details proposing step S20.

Since S10 to S17 overlap with the above description, description thereof will be omitted.

In the data checking step S18, the surgical details proposing unit 333 checks whether data necessary for proposing surgical details has been arranged. Data necessary for proposing surgical details is a sensor voltage value and a potential value of the cochlear microphonic.

The surgical details proposing unit 333 may use either a sensor voltage value or a potential value of the cochlear microphonic to propose selected surgical details or both.

In addition, if it is determined that data necessary for the surgical details proposing unit 333 to propose surgical details has been arranged (OK in S18), the process proceeds to the data accumulation step S19, or if it is determined that necessary data has not been arranged (NG in S18), the process returns to the evaluation item determination step S11.

Next, in the data accumulation step S19, the sensor voltage value, the potential value of the cochlear microphonic, and the surgical details checked in the data checking step S18 are stored in the database 700B.

With respect to the data, the data output in the output step S17 can be stored in the database 700B.

In addition, sensor voltage values and potential values of the cochlear microphonic measured during and after treatment may be stored in the data accumulation step S19.

Furthermore, in the data accumulation step S19, mobility analysis values calculated in numeral simulations and details of symptoms assumed in the analysis may be stored. In this case, mobility analysis values calculated by separately performing separate FEM (finite element method) analysis can be used.

Next, in the surgical details proposing step S20, selected surgical details are proposed on the basis of at least one of the sensor voltage value and the potential value measured before treatment with reference to the sensor voltage values, potential values, and surgical details stored in the database 700B.

Accordingly, a site of the middle ear of the patient for which treatment is to be performed and the method thereof can be selected using data of the stored data which is most similar to the treatment.

In addition, the sensor voltage values and the potential values of the cochlear microphone measured during and after the treatment may be referred to in the data accumulation step.

Accordingly, by immediately evaluating middle ear sound transmission characteristics changing in accordance with the course of the surgery, whether the site of the middle ear of the patient for which treatment has been performed is correct or the details of the treatment are correct can be checked on the spot.

By executing the series of above-described processes, the mobility and vibration transmission efficiency of the ossicles 900 can be quantitatively evaluated during the middle ear surgery performed using the probe 103, and thus the middle ear surgery can be performed while quantitatively determining the degree of hearing restoration.

Furthermore, since the surgical details proposing unit 333 proposes the site to be treated and the method thereof on the basis of the information stored in the database 700B, even if the operator has little surgical experience, adequate surgery can be performed using stored past surgical details and analysis values.

According to the middle ear sound transmission characteristics evaluation system 2 of this example, the database 700B stores the sensor voltage value output by the force sensor before treatment, potential value detected from the electrode 600, and surgical details as described above.

Then, the surgical details proposing unit 333 proposes the selected surgical details on the basis of at least one of the sensor voltage value and the potential value measured before the surgery with reference to the sensor voltage values, potential values, and surgical details stored in the database 700B. Thus, identification of a defective site and selection of treatment become easy by utilizing past surgical experience, and the selected surgical details can be proposed.

In addition, the database 700B includes assumed symptoms and mobility analysis values as the values of the mobility at the time of the symptoms, and the surgical details proposing unit 333 proposes the selected surgical details using the information. Thus, even if there is little accumulation of record values, the selected surgical details can be proposed using the mobility analysis values obtained from numerical simulations.

In addition, the database 700B stores the sensor voltage values and potential values detected from the cochlear microphonic measured during and after the treatment and the surgical details proposing unit 333 proposes the selected surgical details also using the information. Thus, the surgery can be performed while the states of the mobility and vibration transmission efficiency are checked during and after the surgery, a more reliable surgical method can be selected.

In addition, the measuring probe 100B has the fulcrum metal fitting 109C formed to cover the probe 103 from the both sides in the left-right direction, and the rotational shaft 150 that pivotably supports the probe 103 in the top-bottom direction. In addition, the rotational shaft 150 is disposed as if it penetrates the probe 103 and the fulcrum metal fitting 109C. Thus, the probe 103 is constantly connected to the fulcrum metal fitting 109C by the rotational shaft 150, and when the probe 103 vibrates, it is possible to reliably prevent the probe 103 from being removed from the fulcrum metal fitting 109C.

In addition, the measuring probe 100B includes the metal frame 180 including the housing recess in which the fulcrum metal fitting 109C is housed while supporting the probe 103.

Thus, the weight and rigidity of the entire measuring probe 100B can be increased, and the occurrence of vibration that will be noise caused by vibration of the measuring probe 100B resulting from vibration of the actuator 116 can be suppressed.

In addition, the fixing magnet 235 that fixes the fulcrum metal fitting 109C is built into the metal frame 180. Thus, while the fulcrum metal fitting 109C is detachable from the metal frame 180, the metal frame 180 can be held by the fulcrum metal fitting 109C due to the magnetization force of the fixing magnet 235. Accordingly, while easy replacement of the probe 103 is ensured, displacement of the probe 103 can be prevented, and convenience of the measuring probe 100B can be improved.

In addition, the cover having the opening 160 that is formed from which the tip of the probe 103 protrudes outward is provided, and the metal cap 170 is detachably attached to the opening 160 of the cover.

Thus, for example, even when the measuring probe 100B is coated with a sterilizing sheet, the sterilizing sheet covering the upper cover and the lower cover A106 can be fixed to the opening 160 using the metal cap 170 after thermal disinfection is performed only on the metal cap 170.

Accordingly, even when it is difficult to perform thermal disinfection on the entire measuring probe 100B that is constituted by electronic components, the measuring probe can be used in a clean state.

In addition, the measuring probe 100B includes the actuator case 140 that covers the actuator 116, and the inside of the actuator case 140 has a watertight structure. Thus, even in a case where blood or body fluids of a patient hit the probe 103 and enter the inside of the measuring probe 100B during surgery, it is possible to avoid malfunction that may happen to electronic components disposed inside the actuator case 140.

This example is merely illustrative to describe the principle and desired effects, and does not limit this disclosure. Those skilled in the technology can make addition or modification with respect to the example on the premise that it does not depart from the scope of the disclosure. That is, any equivalent addition or modification made by those skilled in the art on the premise that it does not depart from the technical philosophy and belongs to the appended claims.

Although this example has introduced the configuration in which, for example, the surgical details proposing unit 333 proposes the selected surgical details on the basis of at least one of a measured sensor voltage value and potential value of the cochlear microphonic, this disclosure is not limited thereto.

That is, the value of a mobility evaluation level categorized by the mobility evaluation unit 331 may be used as an index indicating the magnitude of a measured sensor voltage value, and the value of a vibration transmission efficiency evaluation level categorized by vibration transmission efficiency evaluation unit 332 may be used as an index indicating the magnitude of a potential value of the cochlear microphonic.

In addition, although this example has introduced the configuration in which the potential of the cochlear microphonic detected by the electrode 600 is amplified in the amplification step S15, the disclosure is not limited thereto. Without performing the amplification step S15, the following steps may be performed using the potential value detected from the cochlear microphonic without change.

In addition, the order of the steps described in this example may be arbitrarily changed within the scope not departing from the scope of this disclosure. That is, a plurality of steps among the above steps may be performed in parallel at the same time.

The present application is a continuation application of International Application No. PCT/JP2018/042525, filed on Jul. 30, 2018. The contents of this application are incorporated herein by reference in their entirety.

The invention claimed is:

1. A middle ear sound transmission characteristics evaluation system comprising:
    a probe;
    a measuring probe that includes an actuator that vibrates the probe and a force sensor that outputs a voltage in accordance with a reaction force exerted to the actuator when a tip of the probe is brought into contact with ossicles;
    an electrode configured to be installed at a round window and to detect a potential value of a cochlear microphonic when vibration is applied to the ossicles by the probe;
    a database that stores a sensor voltage value output by the force sensor before surgical treatment, the potential value detected by the electrode, and surgical details,
    an information processor that proposes selected surgical details on a basis of a magnitude of at least one of the sensor voltage value and the potential value measured before surgery with reference to a plurality of the sensor voltage values, potential values, and surgical details stored in the database; and
    an amplifier that amplifies the detected potential value of the cochlear microphonic;
    wherein the information processor is further configured to:
        categorize mobility of the ossicles into one of a plurality of mobility evaluation levels on a basis of the sensor voltage value output from the force sensor,
        categorize vibration transmission efficiency of the ossicles into one of a plurality of vibration transmission efficiency evaluation levels on a basis of the amplified potential value,
        and output the value of the mobility evaluation level categorized by the information processor and the value of the vibration transmission efficiency evaluation level categorized by the information processor; and
    wherein the database stores the value of the mobility evaluation level and the value of the vibration transmission efficiency evaluation level.

2. The middle ear sound transmission characteristics evaluation system according to claim 1,
    wherein the database stores symptoms assumed in the ossicles and mobility analysis values calculated from numerical simulations as values of mobility at the times of the symptoms, and
    the information processor proposes selected surgical details on a basis of a magnitude of a sensor voltage value measured before surgery with reference to the assumed symptoms and the mobility analysis values stored in the database.

3. The middle ear sound transmission characteristics evaluation system according to claim 1,
    wherein the database further stores sensor voltage values output by the force sensor during and after surgical treatment and potential values detected by the electrode, and
    the information processor proposes selected surgical details on a basis of a magnitude of at least one of measured sensor voltage values and measured potential values with reference to the sensor voltage values, the potential values, and the surgical details stored in the database.

4. The middle ear sound transmission characteristics evaluation system according to claim 1,
    wherein the information processor obtains a magnitude of a specific frequency component of the voltage output from the force sensor and categorizes the mobility of the ossicles into one of the plurality of mobility evaluation levels on the basis of the magnitude.

5. The middle ear sound transmission characteristics evaluation system according to claim 4,
    wherein the actuator vibrates the probe at a frequency of 5 Hz or higher, and
    the information processor sets the specific frequency component as a frequency component of 5 Hz or higher.

6. The middle ear sound transmission characteristics evaluation system according to claim 1,
    wherein the information processor obtains a magnitude of a specific frequency component of the voltage output from the amplifier and categorizes the vibration transmission efficiency of the ossicles into one of the plurality of vibration transmission efficiency evaluation levels on the basis of the magnitude.

7. A middle ear sound transmission characteristics evaluation method comprising:
    an excitation step in which vibration is applied to ossicles by bringing a tip of a probe that has been vibrated by an actuator in contact with the ossicles;
    a voltage measurement step in which a voltage in accordance with a reaction force to the actuator when the tip of the probe is brought into contact with the ossicles is output;
    a cochlear microphonic potential detection step in which a potential value of a cochlear microphonic generated when vibration is applied to the ossicles in the excitation step is detected by an electrode configured to be installed at a round window;
    a data accumulation step in which a sensor voltage value output in the voltage measurement step before surgical treatment, the potential value detected in the cochlear microphonic potential detection step, and surgical details are stored in a database; and
    a surgical details proposing step in which selected surgical details are proposed on a basis of at least one of the sensor voltage value and the potential value measured before surgery with reference to a plurality of the sensor voltage values, the potential values, and the surgical details stored in the database;
    an amplifying step that amplifies the detected potential value of the cochlear microphonic by an amplifier;
    the surgical details proposing step includes;
        a first categorizing step that categorizes mobility of the ossicles into one of a plurality of mobility evaluation levels on a basis of the sensor voltage value output from the force sensor,
        a second categorizing step that categorizes vibration transmission efficiency of the ossicles into one of a plurality of vibration transmission efficiency evaluation levels on a basis of the amplified potential value; and output step that outputs the value of the mobility evaluation level categorized in the first categorizing step and the value of the vibration transmission efficiency evaluation level categorized in the second categorizing step;

wherein the database stores the value of the mobility evaluation level and the value of the vibration transmission efficiency evaluation level.

8. A measuring probe comprising:
a probe;
a fulcrum metal fitting that supports the probe;
an actuator that vibrates the probe; and
a force sensor that outputs a voltage in accordance with a reaction force to the actuator when a tip of the probe is brought into contact with ossicles,
wherein the actuator applies vibration having a constant amplitude with respect to a fulcrum at the center of gravity of the probe,
the force sensor includes a piezoelectric sensor and a charge amplifier,
the piezoelectric sensor converts a reaction force to a force exerted by the actuator via the probe to the ossicles into a charge signal, and
the charge amplifier converts the charge signal into a voltage and outputs the voltage;
wherein the probe is detachably supported by a fixation fulcrum and the force sensor at two points that are respectively at the center of gravity and a base end of the probe,
the probe has a recess formed at the center of gravity, and
the fulcrum metal fitting includes a support that supports the probe while fitting into the recess and attracts the probe using a magnetization force.

9. The measuring probe according to claim 8, wherein the actuator vibrates the probe at a frequency of 5 Hz or higher.

10. The measuring probe according to claim 8, comprising:
a rigidity/inertial force applying member that applies rigidity with which relative positions of the fulcrum and the actuator can be kept constant and an inertial force with which the measuring probe can resist vibration of the actuator to the measuring probe.

11. The measuring probe according to claim 8, comprising:
an elastic body that elastically comes in contact with the probe,
wherein the probe is biased to the support by the elastic body.

12. The measuring probe according to claim 8,
wherein an inner surface of the recess has a spherical surface shape, and
the support has a spherical body shape.

13. The measuring probe according to claim 8,
wherein the probe is detachably supported by the fixation fulcrum and the force sensor at two points that are respectively at the center of gravity and the base end of the probe, an inner surface of the recess has a triangular shape in a longitudinal cross section view in a direction in which the probe extends, and
a part of the fulcrum metal fitting in contact with the recess has a triangular shape in the longitudinal cross section view.

14. A measuring probe comprising:
a probe;
a fulcrum metal fitting that supports the probe;
an actuator that vibrates the probe; and
a force sensor that outputs a voltage in accordance with a reaction force to the actuator when a tip of the probe is brought into contact with ossicles,
wherein the actuator applies vibration having a constant amplitude with respect to a fulcrum at the center of gravity of the probe,
the force sensor includes a piezoelectric sensor and a charge amplifier,
the piezoelectric sensor converts a reaction force to a force exerted by the actuator via the probe to the ossicles into a charge signal, and
the charge amplifier converts the charge signal into a voltage and outputs the voltage;
wherein the fulcrum metal fitting is formed to cover the probe from both sides in a left-right direction,
a rotational shaft that extends orthogonally to the probe in a top view and pivotably supports the probe in a top-bottom direction is provided, and
the rotational shaft is disposed to penetrate the probe and the fulcrum metal fitting.

15. The measuring probe according to claim 14, comprising:
a metal frame including a housing recess in which the fulcrum metal fitting is housed while supporting the probe,
wherein a fixing magnet that fixes the fulcrum metal fitting is built into the metal frame.

16. The measuring probe according to claim 14, further comprising:
a cover having an opening formed to allow the tip of the probe to protrude outward,
wherein a pipe-shaped metal cap coaxially formed with the opening is detachably attached to the opening.

17. The measuring probe according to claim 14, further comprising:
an actuator case that covers the actuator,
wherein an inner side of the actuator case has a watertight structure.

18. The measuring probe according to claim 14, wherein the actuator vibrates the probe at a frequency of 5 Hz or higher.

19. The measuring probe according to claim 14, comprising:
a rigidity/inertial force applying member that applies rigidity with which relative positions of the fulcrum and the actuator can be kept constant and an inertial force with which the measuring probe can resist vibration of the actuator to the measuring probe.

* * * * *